US010215687B2

(12) United States Patent
Haghgooie et al.

(10) Patent No.: US 10,215,687 B2
(45) Date of Patent: Feb. 26, 2019

(54) METHOD AND SYSTEM FOR INTEGRATED MUTLIPLEXED PHOTOMETRY MODULE

(71) Applicant: THE GENERAL HOSPITAL CORPORATION, Boston, MA (US)

(72) Inventors: Ramin Haghgooie, Arlington, AR (US); Kenneth T. Kotz, Auburndale, MA (US); Robert Granier, Boston, MA (US); Anne Celia Petrofsky, Sudbury, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/677,459

(22) Filed: Aug. 15, 2017

(65) Prior Publication Data

US 2018/0088025 A1  Mar. 29, 2018

Related U.S. Application Data

(63) Continuation-in-part of application No. 14/443,915, filed as application No. PCT/US2013/070555 on Nov. 18, 2013, now Pat. No. 9,759,649.
(Continued)

(51) Int. Cl.
*G01N 21/03* (2006.01)
*B01L 3/00* (2006.01)
(Continued)

(52) U.S. Cl.
CPC ........... *G01N 21/03* (2013.01); *B01L 3/5027* (2013.01); *G01N 21/11* (2013.01); *G01N 21/253* (2013.01);
(Continued)

(58) Field of Classification Search
CPC .............. G01N 21/05; G01N 21/27; G01N 2021/0346; G01N 2021/0378;
(Continued)

(56) References Cited

U.S. PATENT DOCUMENTS 7,745,221 B2    6/2010   Butler et al.
8,337,777 B2 *  12/2012  Nurse ............... B01L 3/502738
                                                137/15.06
(Continued)

*Primary Examiner* — Sang H Nguyen
(74) *Attorney, Agent, or Firm* — Quarles & Brady LLP; Yakov S. Sidorin

(57) ABSTRACT

Reusable network of spatially-multiplexed microfluidic channels each including an inlet, an outlet, and a cuvette in-between. Individual channels may operationally share a main or common output channel defining the network output and optionally leading to a disposable storage volume. Alternatively, multiple channels are structured to individually lead to the storage volume. An individual cuvette is dimensioned to substantially prevent the formation of air-bubbles during the fluid sample flow through the cuvette and, therefore, to be fully filled and fully emptied. The overall channel network is configured to spatially lock the fluidic sample by pressing such sample with a second fluid against a closed to substantially immobilize it to prevent drifting due to the change in ambient conditions during the measurement. Thereafter, the fluidic sample is flushed through the now-opened valve with continually-applied pressure of the second fluid. System and method for photometric measurements of multiple fluid samples employing such network of channels.

27 Claims, 18 Drawing Sheets

Related U.S. Application Data

(60) Provisional application No. 61/727,817, filed on Nov. 19, 2012.

(51) Int. Cl.
*G01N 21/11* (2006.01)
*G01N 21/25* (2006.01)

(52) U.S. Cl.
CPC ............... *G01N 2021/0346* (2013.01); *G01N 2021/0357* (2013.01)

(58) Field of Classification Search
CPC ...... G01N 2021/054; G01N 2021/0357; B01L 3/502723; B01L 3/502746; B01L 2200/027; B01L 2200/0684; B01L 2200/141
See application file for complete search history.

(56) References Cited

U.S. PATENT DOCUMENTS

| | | | |
|---|---|---|---|
| 8,535,536 B1* | 9/2013 | Gale | B01D 57/00 210/198.1 |
| 8,557,518 B2 | 10/2013 | Jovanovich et al. | |
| 9,211,539 B2 | 12/2015 | Amin et al. | |
| 2002/0097632 A1 | 7/2002 | Kellogg et al. | |
| 2005/0105077 A1 | 5/2005 | Padmanabhan et al. | |
| 2005/0266582 A1* | 12/2005 | Modlin | B01L 3/5027 436/164 |
| 2007/0003434 A1 | 1/2007 | Padmanabhan et al. | |
| 2007/0014695 A1 | 1/2007 | Yue et al. | |
| 2007/0280857 A1 | 12/2007 | Song et al. | |
| 2008/0118369 A1 | 5/2008 | Sando et al. | |
| 2008/0273918 A1 | 11/2008 | Linder et al. | |
| 2009/0051901 A1 | 2/2009 | Shen et al. | |
| 2012/0309648 A1 | 12/2012 | Tseng et al. | |
| 2014/0141438 A1 | 5/2014 | Song et al. | |
| 2014/0174160 A1* | 6/2014 | Michienzi | G01N 30/16 73/61.55 |
| 2016/0003729 A1* | 1/2016 | Lo | G01N 15/1459 435/288.7 |

* cited by examiner

Egress for fluidic sample(s)

Sample Volume

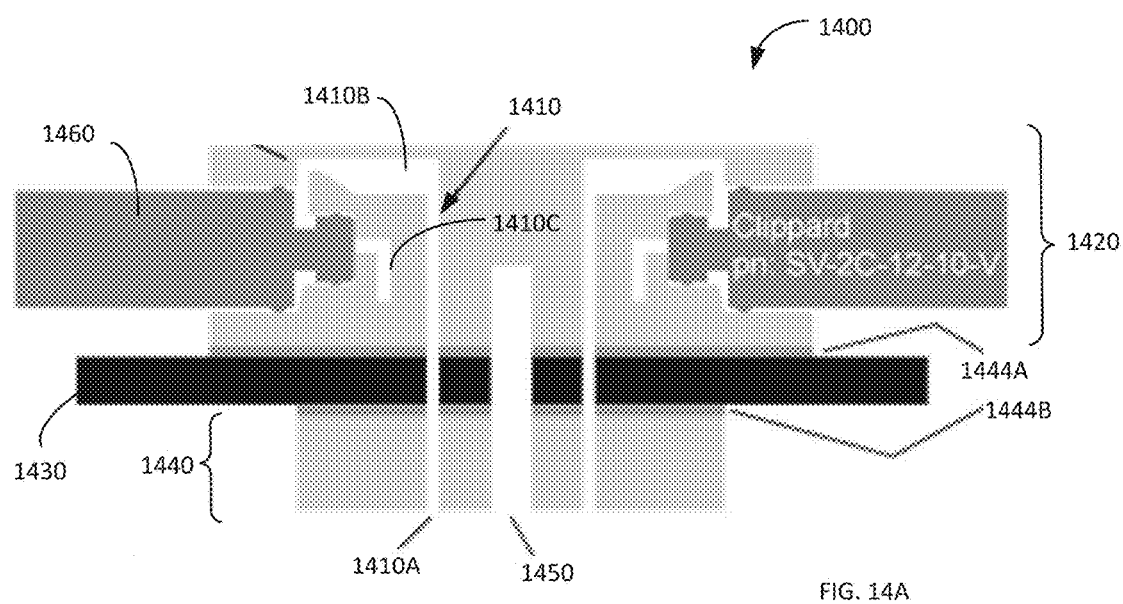
FIG. 14A
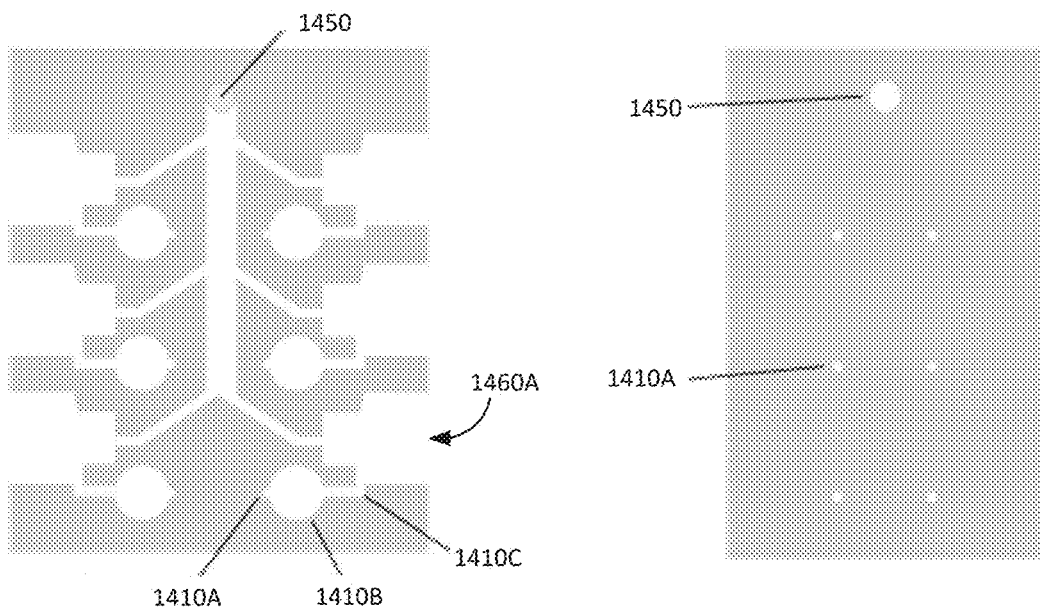
FIG. 14B
FIG. 14C

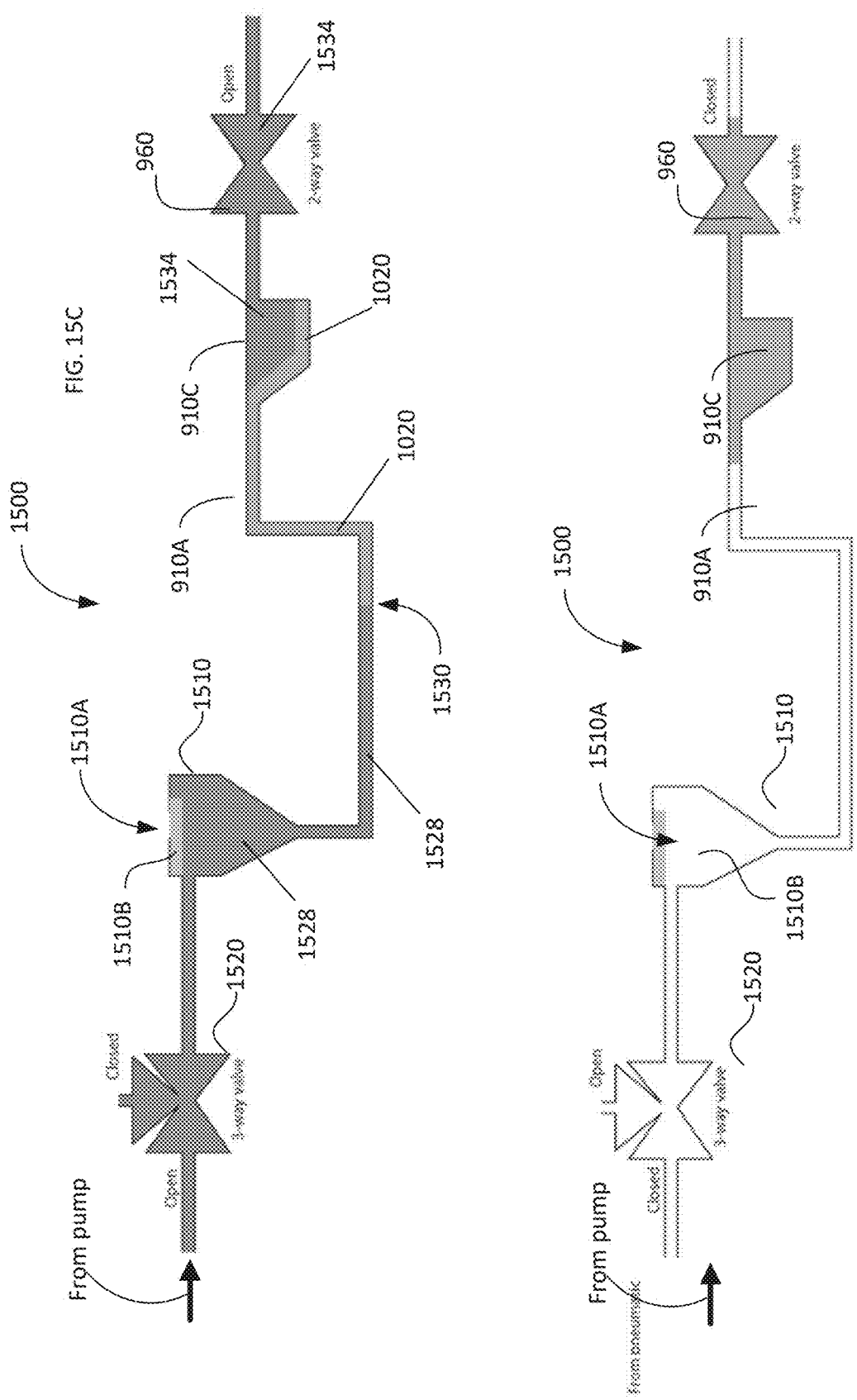

METHOD AND SYSTEM FOR INTEGRATED MUTLIPLEXED PHOTOMETRY MODULE

CROSS-REFERENCE TO RELATED APPLICATIONS

This application is a continuation-in-part of the U.S. patent application Ser. No. 14/443,915, filed on May 19, 2015 and now published as US 2015/0285731, which represents the national stage entry of PCT International Application No. PCT/US2013/070555 filed on Nov. 18, 2013, which in turn claims priority from and benefit of the U.S. Provisional Patent Application No. 61/727,817, filed on Nov. 19, 2013 and titled "INTEGRATED MULTIPLEXED PHOTOMETRY MODULE." The disclosure of each of the abovementioned applications is incorporated by reference herein.

TECHNICAL FIELD

The present invention relates generally to systems and methods for conducting chemical, biochemical, and/or biological assays on a sample and, more particularly, to multiplexed optical spectroscopy performed on samples in microfluidic chambers.

BACKGROUND

Microfluidic devices and systems utilizing such devices employ small capillaries and/or microchannels and/or cuvettes associated or even integrated with a solid substrate to perform a variety of operations in analytical chemical and biochemical applications on a very small scale. The small dimensionality of these systems facilitates sample processing (such as sample transport, analyte enrichment, reaction rate, etc) that uses less reagent volume and that takes up far less laboratory or industrial space. Microfluidic systems thus offer the potential for attractive gains in efficiency of operation, and, consequently, substantial economic advantages.

A variety of spectroscopic techniques can be employed in conjunction with microfluidic devices, including those utilizing infrared (IR) radiation, visible light, and/or ultraviolet (UV) radiation, such as light-scattering spectroscopy, for example. In research or industrial settings, microfluidic devices are typically employed in biochemical or cell-based assays that use spectroscopic detection systems to quantify labeled or unlabeled molecules of interest. Microfluidic devices generally employ networks of integrated microscale channels and reservoirs (with the use of which fluid samples materials are transported, mixed, separated and detected), and various optical systems that are embedded or externally arranged/coordinated with such networks for optical recognition, detection, quantification, as well as other manipulations of the fluidic samples.

There exists an unsatisfied need in such expansion of the assay menu capacity of a microfluidic photometric system that would manifest in the reduction of volume of a liquid sample (required for the photometric measurement) as well as improving the accuracy and precision of the photometric measurement itself. Point of care integrated blood analysis instruments and environmental monitoring instruments are but two examples of devices that would benefit from such expansion.

There also exists an unsatisfied need for a low per test cost (reusable, small volume) photometry system capable of performing a variety of biochemical assays (mutliplexing) from a single sample at the point of care. The need of operable integration of such system with other complimentary analytical systems such as flow cytometry system to further simplify testing (by, for example, elimination of multiple instruments/samples), capture economies of scale and scope (to reduce the overall cost) and enable decision making (for example, to obtain comprehensive test data from a single sample) remains not addressed.

SUMMARY

Embodiments of the present invention provide a method for performing a photometric measurement. The method includes the steps of (i) transmitting light from a first light source to a first photodetector through a corresponding first cuvette containing a first fluid sample delivered to the first cuvette from a corresponding first inlet; and (ii) transmitting light from a second light source to a second photodetector through a corresponding second cuvette containing a second fluid sample delivered to the second cuvette from a corresponding second inlet. The method also includes the step of acquiring data representing the first and second fluid sample while at least one of the first and second fluid samples is prevented from being displaced, with respect to a respectively-corresponding cuvette, by (a) closing a respectively-corresponding valve in fluid contact with the at least one of the first and second fluid samples on a first side of the respectively-corresponding cuvette, and (b) having the at least one of the first and second fluid samples under pressure on a second side of the respectively-corresponding cuvette, where such pressure is formed by a second fluid in contact with the at least one of the first and second samples. The closing of the valve may be effectuated while a corresponding fluid sample is under the above-specified pressure. The method further includes a step of removing the first and second fluid samples from the first and second cuvettes through respectively-corresponding first and second outlets by opening respectively-corresponding valves at the first and second outlets while maintaining the pressure. The first and second cuvettes are dimensioned to substantially prevent a formation of air-pockets therein while the first and second fluid samples flow therethrough. Alternatively or in addition, the first and second cuvettes are dimensioned to minimize fluid-sample-to-fluid-sample carry-over due to said removing and subsequent filling of any of the first and second cuvettes to not materially influence results of a subsequent step of acquisition of data representing another sample measured in the same cuvette.

Embodiments of the invention also provide a related method for performing a photometric measurement. The method includes temporarily stopping a flow of a first fluid sample through a first cuvette of a first microfluidic channel of a microfluidic chip, for a first duration sufficient to carry out a first photometric measurement of an analyte in the first fluid sample, to immobilize the first fluid sample and to prevent a first displacement of the first sample with respect to the first cuvette. Here, the microfluidic chip is structured to contain multiple substrates integrated with one another along their corresponding surfaces to form an interface. The method further includes carrying the photometric measurement by:

(i) transmitting light from a first light source to a first photodetector through the first cuvette containing said first fluid sample that has been delivered to the first cuvette from a first inlet through a first inlet channel that extends through the interface; and
(ii) while the first displacement is prevented, acquiring first data from the first photodetector, said first data representing said first fluid sample. Furthermore, the method includes a step of completely removing the first fluid sample from the first cuvettes through a first outlet channel and a first fluidic valve operably cooperated with the first outlet channel.

Embodiments of the invention also provide a microfluidic device that contains first and second substrates integrated with one another along surfaces thereof to form a stack of substrates; a first microfluidic channel including first inlet portion, first cuvette portion, and first outlet portion (here, at least one of said first inlet and outlet portions traverses both of the first and second substrates); a first fluidic valve in fluid communication fluidly connected to the outlet portion; a fluidic well disposed upstream with respect to the first cuvette portion in fluid communication with the first inlet portion. Here, the well has an internal volume and an aperture or orifice connecting the internal volume with an ambient medium surrounding the well. The well is equipped with a flap element dimensioned to reversibly close the aperture from inside the well when in a rest position, and to reversibly open said aperture in response to a force applied to the flap element from the ambient medium inwardly to the internal volume.

BRIEF DESCRIPTION OF THE DRAWINGS

The invention will be more fully understood by referring to the following Detailed Description in conjunction with the Drawings, of which:

FIG. 13A: cross-sectional view of the system; FIG. 13B: top view of the fluidic manifold portion of the system.

FIGS. 14A, 14B, and 14C provide schematics describing an embodiment of a multiplexed photometer system with internal valving, that has the only, single outlet in the photometer. FIG. 14A: cross-sectional view of the system; FIG. 14B: top view of the multiplex photometer module of the system; FIG. 14C: top view of the fluidic manifold portion of the system.

FIGS. 15A, 15B, 15C, 15D, 15E, 15F, 15G, and 15H provide additional diagrams illustrating the structure and principle of operation of an embodiment of the invention.

Figure 1A:
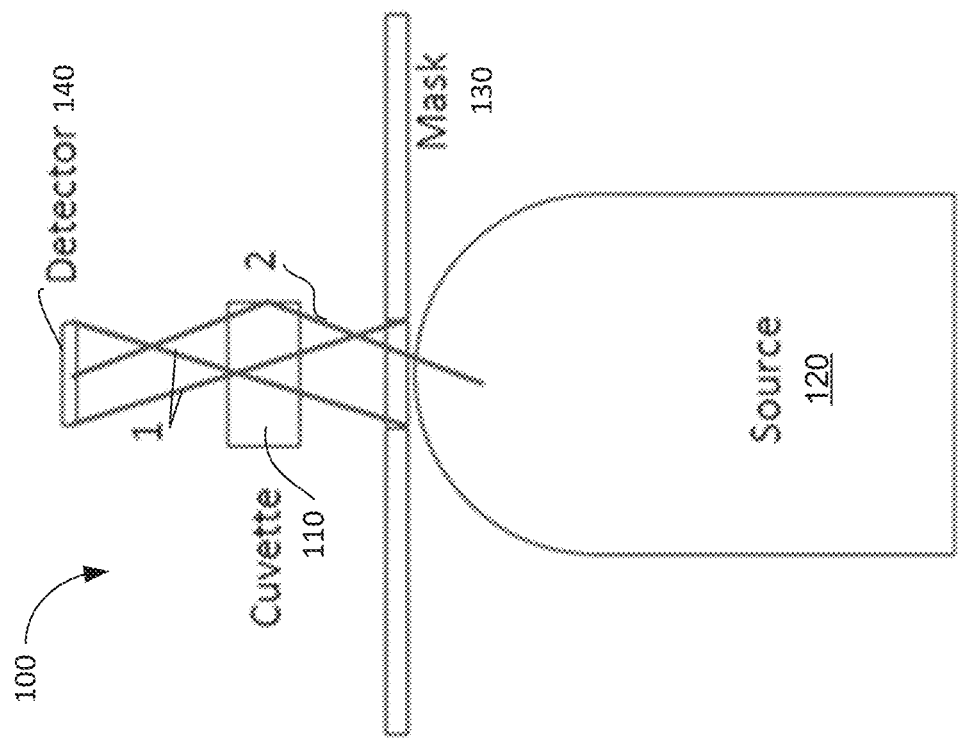
FIGS. 1A and 1B are perspective and plan view illustrations of a simplified photometric microfluidic system employing a single cuvette.

The sizes and relative scales of elements in Drawings may be set to be different from actual size and scales to appropriately facilitate simplicity, clarity, and understanding of the Drawings. For the same reason, not all elements present in one Drawing may necessarily be shown and/or labeled in another.

DETAILED DESCRIPTION

In accordance with an idea of the present invention, a microfluidic cuvette component of a network of microfluidic channels used in a photometric module of the invention is structured such as to be substantially completely filled and flushed, in operation, without leaving a volume of fluid that would substantially influence a subsequent measurement performed in the same fluidic network. Implementations of such cuvettes are many, including, for example, sample metering and/or conditioning. In this case, a cuvette (also interchangeably referred to as a chamber) is used to isolate a repeatable well defined volume of sample for further downstream processing by, for example, appropriately incorporating fluidic valves up-stream and down-stream with respect to the chambers to isolate the sample prior to processing. In another application, referred to herein as "volume sensing", an individual cuvette or chamber (that is adapted to be filled and emptied substantially completely) is used to determine when a particular volume of fluid has been introduced into the system. Such volumes sensor could be placed at the outlet of the cuvette or chamber such that when the chamber is filled, the sensor is triggered generating an indicator that the target volume has been reached. Used in any of such applications, an embodiment of the invention is configured such as to ensure that the isolated is the cuvette volume of fluidic sample is spatially still/fixed/immobilized with respect to a corresponding channel/cuvette during the photometric measurement. This solution is provided, in part, by appropriately operating a fluidic valves on one side of the cuvette to isolate the sample from the fluidic pressure downstream with respect to the cuvette. Alternatively, the solution is provided by appropriately operating a fluidic valve on one side of the cuvette while, at the same time, locking the fluidic sample of interest in place with the use of pressure applied (with the use of a different fluid) to a front end and/or back end of the fluidic sample.

While the proposed cuvette element is operable and usable on its own, a fluidic network of channels containing such fully fillable-and-emptied cuvettes is also implemented. The network is adapted to operationally isolate the individual cuvettes contained in different branches of the network, is also implemented for use different applications including, for example, drug screening, facilitation of multi-reagent chemical reactions, and photometric measurements. In the case of drug screening for example, the proposed fluidic network is adapted to differentiate among individual cell cultures in a multiplexed cell culture sample. An example of the fluidic network employs an array of cell culture chambers that can be individually stimulated with different chemicals but share a common outlet. So designed network is configured to prevent cross-talk between the chambers, keeping each one in isolation. In another implementation, the proposed fluidic network facilitates multi-reagent chemical reaction processes by isolating different components of a chemical reaction from one another. When different branches of the fluidic network are flushed, the reaction would be initiated only in the common waste stream. In this manner, the order in which reagents are added to the reaction solution are controlled, thereby facilitating the control over the reaction products.

Related embodiments disclose examples of a microfluidic photometric apparatus configured, according to the idea of the invention, to take advantage, in operation, of an individual cuvette and/or of the proposed fluidic network. An implementation of the photometric apparatus has a multi-plexed cuvette unit that is structured for repeatable and volumetrically uniform fill-fix-in-space-measure-flush-and-re-use operation substantially without forming air bubbles in the cuvette while, at the same time, providing sample aliquots with geometrical constraints defined in such a fashion as to ensure that a pathlength of light traversing the cuvette installed in the photometric apparatus is substantially invariant.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention, in other words, a given drawing is generally descriptive of only some, and not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in the appended claims is intended to be assessed in light of the disclosure as a whole.

Photometric and radiometric methodologies (aggregately referred to, for the purposes of this disclosure, using such terms as "photometry" and "photometric", which includes fluorometric measurements such as performing immunoassays using micro particles—Chemiluminescent Microparticle Immunoassay or CMIA—as the antibody/analyte binding substrate) have been widely adopted as tools for determining concentrations of analytes in both human and animal biological samples such as, for example, blood, urine, and saliva, to name just a few. (Photometric methods can also be used for environmental testing. For instance, groundwater can be tested for contamination due to various chemical species.) In vitro diagnostic devices using photometric detection techniques have been developed for a large variety of clinical biomarkers. In general, there are three classes of reaction schemes for clinical assays that are evaluated using photometric methods.

Chemical endpoint reactions involve the complete conversion of an analyte using synthetic chemicals. The conversion results in a change in absorbance of the sample, which is measured after the reaction has completed. The final absorbance of the sample is proportional to the analyte concentration. Some analytes, the concentrations of which are determined with chemical endpoint assays, include hemoglobin, calcium, and total protein.

Enzymatic endpoint reactions also involve the complete conversion of an analyte, such as glucose, for example. However in this case, the conversion is catalyzed by the presence of an enzyme. The absorbance of the sample is, again, measured after the reaction is completed and is proportional to the analyte concentration. Analytes the concentrations of which are determined with enzymatic endpoint reactions include creatinine, glucose, and bilirubin.

Enzymatic rate reactions involve the continuous conversion of an analyte catalyzed by an enzyme. Absorbance of a sample in this case is monitored over time, and the rate of change of absorbance is proportional to the concentration of an analyte. Enzymatic rate reactions normally require tight temperature control to ensure that the reaction rate remains constant over the course of the measurement. Analytes the concentrations of which are determined with enzymatic rate reactions include alkaline phosphatase (ALP), alanine aminotransferase (ALT), and chloride.

Based on Beer's law, according to which the absorption of light in a sample is proportional to the concentration of the analyte, the absorbance of light $A_X^\lambda$ at wavelength $\lambda$, caused by the presence of species X at a concentration [X] along a path L through the sample, can be expressed as $$A_X^\lambda = \varepsilon_X^\lambda [X] L = \log_{10}\left[\frac{I_0}{I}\right] \qquad \text{Eq.(1)}$$

where $\varepsilon_X^\lambda$ is the millimolar absorptivity of the species X at the designated wavelength. Accordingly, the concentration of the sought-after species can be expressed as $$[X] = \log_{10}\left[\frac{I_0}{I}\right] / (\varepsilon_X^\lambda L) \qquad \text{Eq. (2)}$$

The transmitted through the sample radiant power is determined by integrating the light intensity transmitted by the sample over a range of wavelengths of interest and multiplying by the sensitivity of the detector at those wavelengths. This can be accomplished in several ways. A broad spectrum light source may be used with a spectrophotometer as a detector which splits the transmitted light into component wavelengths that are individually detected and can be read at the wavelengths of interest. Alternatively, a narrow band wavelength light source may be used with a single point detector to absorb all of the transmitted light.

Generally, the terms "sample", "biological sample", "chemical sample" and the like as used herein refer to a sample of fluid material that is assumed to contain an analyte of interest. For example, samples include various fluids such as various solutions, bodily fluids (such as whole blood, serum, plasma, cerebrospinal fluid, urine, lymph fluids), and other fluids (such as, for example, cell culture suspensions, cell extracts, cell culture supernatants). A sample may be suspended or dissolved in, for example, buffers, extractants, solvents, and the like. Additional examples of samples are provided by fluids deliberately created for the study of biological processes or discovery or screening of drug candidates. The latter include, but are not limited to, aqueous samples that have been doped with bacteria, viruses, DNA, polypeptides, natural or recombinant proteins, metal ions, or drug candidates and their mixtures.

Conventionally, to conduct optical spectroscopic and/or photometric analysis, a sample should be placed in a cuvette that is used and replaced after the measurement is complete.

The currently employed microfluidic cuvettes possess shortcoming that substantially limit their application in a multiplexed photometric system.

Indeed, conventional large scale systems use "open" cuvettes in which solution is directly pipetted into the cuvette (and not flown in through a permanently connected channel). These cuvettes are cleaned out after each use and reused with a cleaning solution via a robotic pipette. Alternatively, conventional point of care systems, which house the cuvette in a single use consumable, the cuvette is discarded at each use. The embodiments of the invention discussed below provide the solutions employing a "flow in and through", reusable cuvette), leading to the advantage of lower consumable cost with respect to traditional POCT photometry systems. With respect to the open cuvette design of larger conventional systems, the proposed below "flow through" system eliminates the need to transport the sample to the cuvette robotically and requires a much smaller footprint.

In addition, in a multiplexed microfluidic photometric system adapted to perform parallel photometry measurements on multiple, generally different analytes, a cuvette volume is an important figures of merit. The smaller the volume of a cuvette, the higher the degree of system and measurement multiplexing is possible for a given "footprint" of the device and the smaller the required sample volume. The term footprint, as used in this disclosure, would be readily understood—unless expressly defined otherwise—as an area of normal projection of a given component or element of the system onto a chosen plane. In order to make measurements of the sample reproducible, a cuvette must have a very well-defined thickness or length (which translates to a well-defined sample path length through the cuvette). The path length of the cuvette determines the measureable concentration of an analyte for the instrument. Accordingly, there is a need for a cuvette that is configured to ensure that the corresponding sample path length accommodates the entire range of concentrations of interest.

In addition, a microfluidic cuvette must be configured such that, in operation, it is completely filled with the sample at hand without introducing air bubbles that obscure the optical path of light used for photometric measurements. Air in the path of light leads to light diffraction, thereby causing errors in measurement of light absorbance.

Moreover, a cuvette is desired that lends itself to being re-used—in contradistinction with replaceable cuvettes of the related art devices—and, therefore, "flushed" to sufficiently remove the just-used/measured fluid sample to ensure that no substantial sample-carryover from one measurement to another. The latter requirement arises from a need to ensure that no sample-carryover contamination occurs from one measurement to the next.

The present invention stems from the realization that the above-mentioned industrial needs are addressed with a microfluidic device configured to include a multiplicity of unidirectional-flux cuvettes that share a common fluidic outlet, are devoid of valves, are dimensioned to substantially eliminate air-bubble formation in a flow of fluid through each of the cuvettes, and that are subject to positive pressure facilitating substantially complete removal of the sample residue and, therefore, use and reuse of the same microfluidic chip.

Figure 1B:
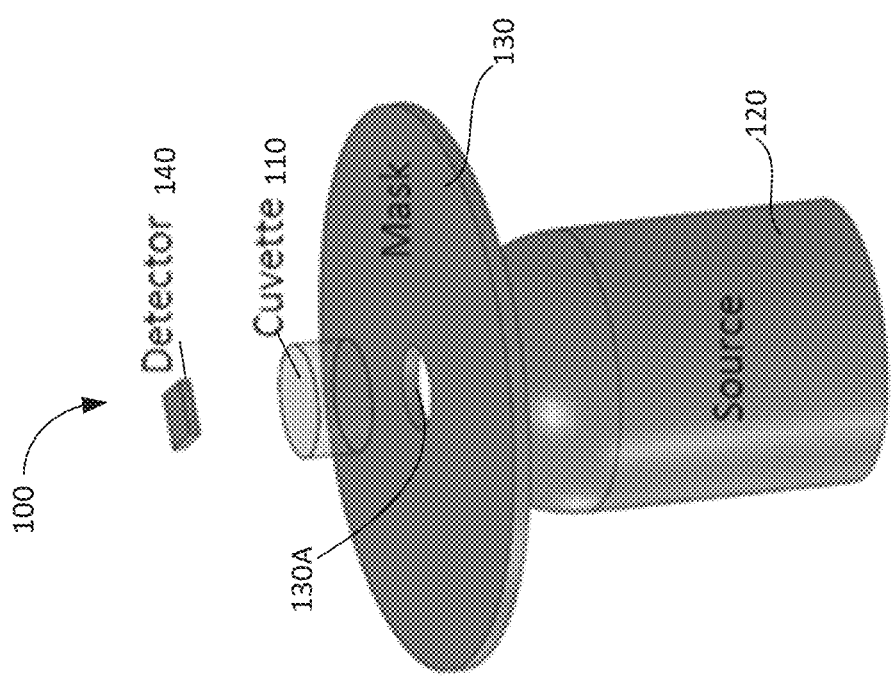

FIGS. 1A and 1B provide perspective and plan view illustrations of a simplified photometric microfluidic system 100 employing a single cuvette 110, providing a conveyor or container for a fluid sample (not shown) that is interrogated with light emanating from the light source 120. Light from the source 120 passes through a spatial mask 130 having an aperture 130A. In reference to FIG. 1A, light propagating between the source of light 120 and the cuvette 110 along path 1 is transmitted directly through the aperture 130A on its way to a detector 140, while light following path 2 is shown to interact with (reflect off of) a side of the cuvette 110. In one implementation, the source of light 120 includes a 5 mm diameter LED, the opening 130A of the approximately 0.3 mm thick mask 130 has a diameter of about 1.5 mm, a chamber of the cuvette 110 has a diameter of about 2 mm and thickness of about 1 mm, while the area of the detector 140 is about 1 mm$^2$.

Figure 2:
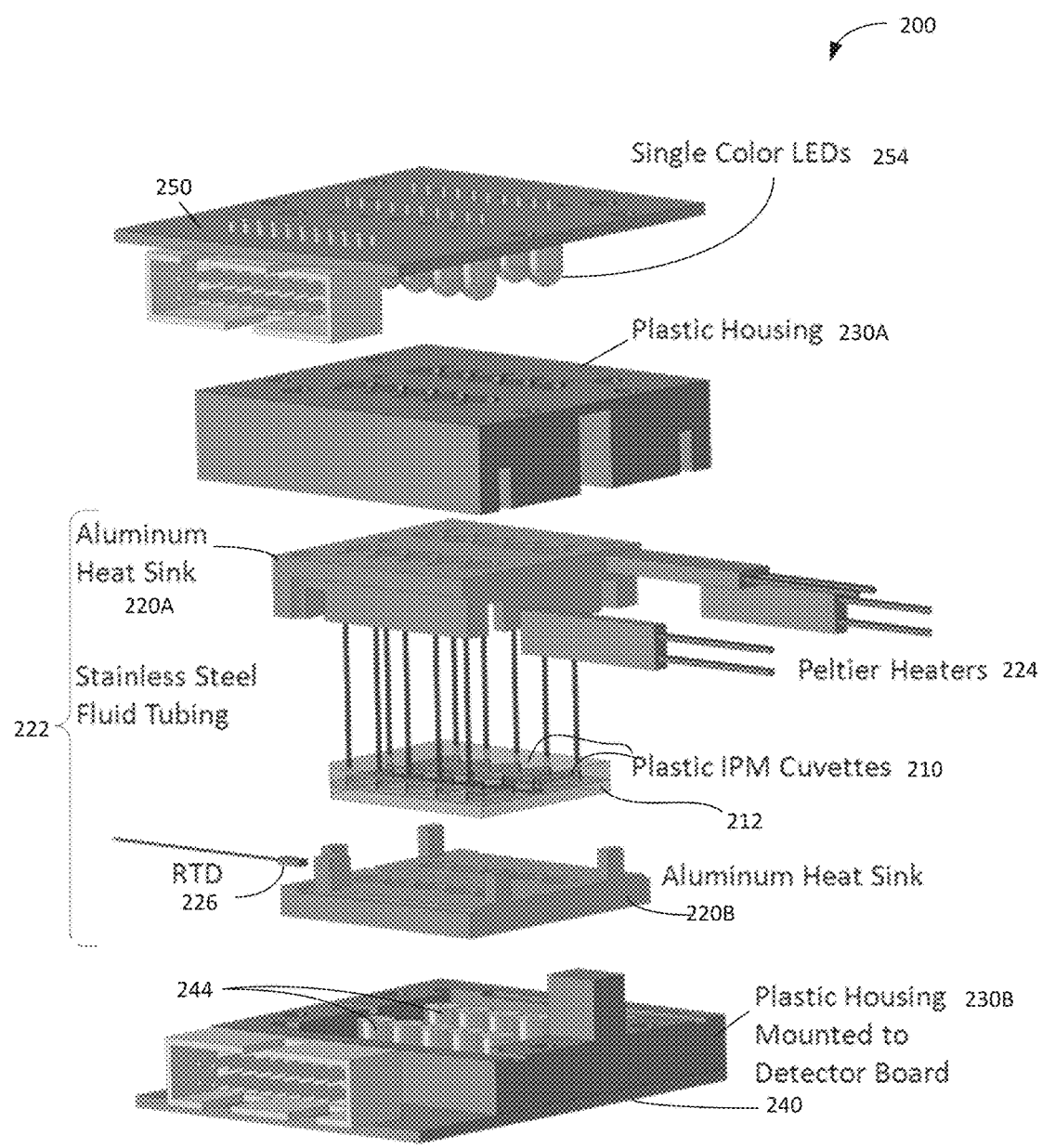
FIG. 2 is an exploded perspective view of an embodiment of the integrated photometric module of the invention.

As another preliminary matter, FIG. 2 provides an exploded perspective view of a simplified embodiment of a photometry module (IPM) according to an embodiment 200 of the invention that employs a multiplicity of individually addressable cuvettes 210 (at least some of which may be similar to the cuvette 110 of FIGS. 1A, 1B). The cuvettes 210, configured for multiplexed photometry measurements, are disposed in association with a polymeric chip 212 and share a common waste outlet, while each of the individual cuvettes 210 includes a circularly-shaped chamber, as discussed in detail below. The IPM cuvette-chip 212 is housed in association with an aluminum housing 220A, 220B that is used as a heat sink to maintain a constant temperature of the system. The system 222 (including the chip 212 and the sink elements 220A, 220B) is heated with Peltier heaters 224 located, as shown, around the exterior of the aluminum heat sink housing 220A, 220B. The temperature of the system is monitored with a resistance temperature detector 226 (RTD) located within the bounds of the heat sink 220A, 220B in contact with the polymeric chip 212. A feedback control loop (not shown) is employed to maintain the system at a constant temperature.

The heat sink 220A, 220B (with all the enclosure thereof) is disposed inside a plastic housing 230A, 230B configured to insulate the system from the environment. A circuit board 240 containing an array of photodiodes 244 (such as, for example, an array of individual single-point photodiodes in T 1¾ packages) is mounted on one side of the plastic housing. In one implementation, the number N of photodiodes equals that of the cuvettes 210. The photodiodes may have, for example, square detectors with active areas of about 1 mm×1 mm and be protected by flat optical windows. A complementary circuit board 250 containing a corresponding number N of narrow-band (or substantially single-wavelength) LEDs 254 in T 1¾ packages with lensed tops is mounted on the other side of the plastic housing 230A.

As an option, a spatial mask (such as the mask 130 of FIGS. 1A, 1B, for example) can be used to limit the area of light incident on the detectors 244 from the light source 254 through the cuvettes 210. In one embodiment, a substantially opaque at the wavelength(s) of interest mask layer can be sandwiched between the cuvette chip 112 and the aluminum heat sink portion 220A such as to have the apertures spatially aligned with the individual cuvettes 210.

Optimization of a Single-Cuvette-and-Channel Geometry

It is appreciated that optimization of the operation of a microfluidic system depends, at least in part, on the ability of a user to utilize a sample of a limited volume. To achieve such optimized operation, the volume of the cuvette should not contain 'dead space' that is filled with the substance of the sample but is not taking part in a photometric measurement. The required operational footprint of the cuvette, which facilitates elimination of such 'dead space', relates to the area of the photodetector used for photometric measurements. In other words, the cuvette should be dimensioned such that every portion of light collected by the photodetector has passed through the cuvette and that path length of such light through the cuvette is substantially the same for any portion of the collected light. If this condition is not observed, the background noise associated with the measurement is increased and the measurements system will have reduced sensitivity at the lower end of the sample-concentration range.

Another factor restricting configuration of a photometric system is a path length, for light propagating from a source of light through the sample being measured to a detector. Typical microfluidic photometric systems are structured to ensure that such path length is on the order of 1 cm. Some point-of-care blood analysis instruments, however, may be configured to utilize path lengths as small as a few hundred microns.

In further reference to FIG. 2, the entire operational volume $V_{sys}$ of a multiplexed photometric system is calculated as $$V_{SYS} = NAL + V_C \qquad \text{Eq. (3),}$$

where N is the number of cuvettes 210, A is the required area (footprint) of a single cuvette, L is the thickness of a single cuvette, and $V_C$ is the volume of a network of channels adapted to provide feeding of the sample to the cuvettes 210 and removal of the waste from the cuvettes (and referred to as feeder-waste channel network, for simplicity). The concentration of a diluted sample is given by $$[X] = [X]_S(1+D) \qquad \text{Eq. (4),}$$

Where the concentration of an undiluted sample is $[X]_S$ and the dilution ratio of the sample assay is defined as D. Based on Eqs. (1) and (4), $$A_X^\lambda = \varepsilon_X^\lambda [X]_1 L_1 = \varepsilon_X^\lambda [X]_2 L_2 \qquad \text{Eq. (5A)}$$

$$[X]_2 = [X]_1 (L_1/L_2) \qquad \text{Eq. (5B)}$$

and, in order to maintain a value of sample absorbance that remains invariant as the cuvette thickness changes, the dilution ratio D must also change as a function of the thickness of the cuvette:

$$D_2 = (L_2/L_1)(1+D_1) - 1 \qquad \text{Eq. (6)}$$

If the overall operational volume of the system is equal to the volume of the diluted sample, the volume $V_S$ of the undiluted sample corresponding to the entire operational volume $V_{sys}$ is determined as $$V_{SYS} = V_S(1+D) \qquad \text{Eq. (7)}$$

Assuming that a pathlength of light and the sample dilution ratio, corresponding to a chosen reference measurement method, are $L_R$ and $D_R$, respectively, the required volume $V_S$ of the undiluted sample is determined, from Eqs. (3), (5A, 5B), (6), and (7), to be reciprocal to the cuvette thickness L:

$$V_S = L_R(NAL + V_C)/(L + LD_R) \qquad \text{Eq. (8)}$$

Overall, the minimum operational value of the cuvette thickness is determined both by the necessity to measure the lowest concentration analyte (at the dilution ratio of the assay) and by the availability of the sample to be measure. As the cuvette thickness decreases, the necessary sample dilution ratio for an assay decreases. If the dilution ratio of the sample is too low, there may not be enough volume of sample to fill a multiplexed cuvette system.

Geometry of an entrance portion of the microfluidic network (for example, a feeder channel that leads to the cuvette) and that of an exit portion of the network (a waste channel following the cuvette) are additional factors defining the efficiency of operation of the microfluidic system.

In reference to FIGS. 3A, 3B, 4A, and 4B, to ensure that no air bubbles are trapped and/or present in a cuvette filled with the substance of the sample and that the fluid flowing through the cuvette maintains a continuous streamline along the wall, a surface defining a wall of the cuvette must be sufficiently smooth and define a tangent described by a continuous function. In a specific embodiment, a wall of the cuvette is defined by a surface that is differentiable (that is, has a derivative) at any point along the wall.

Figure 3A:
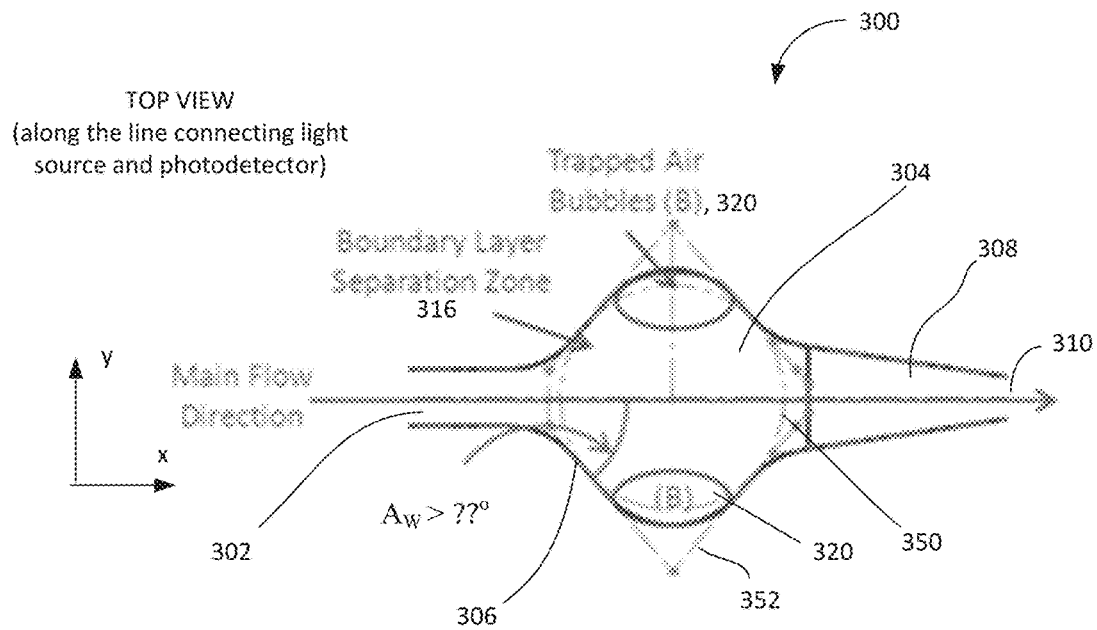
FIGS. 3A and 3B are views of an embodiment, the configuration of which facilitates formation of air-bubbles inside a microfluidic cuvette.
Figure 3B:
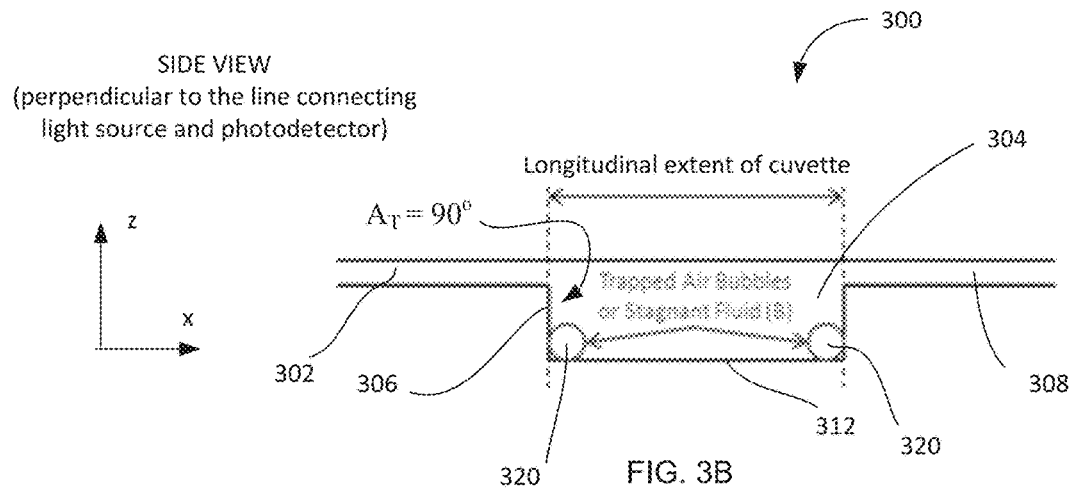

FIGS. 3A and 3B illustrate, not to scale, top and side views, respectively, of an embodiment 300 of a microfluidic network portion including a feeder channel 302, a cuvette 304 with a wall 306, and a waste channel 308. In order to reduce the 'dead' volume, the fluidic channels that feed and empty the cuvette should be as small as possible. The cuvette 304 has an approximately rectangular profile defined by a substantially step-like transitions between a chamber of the cuvette 304 and the feeder/waste channels 302, 308 in a cross-sectional plane that is parallel to both the main direction 310 of fluid sample flow and the direction of propagation of light (shown as axis z in FIG. 3B). In particular, the transition angle $A_T$ between the wall 306 and the bottom 312 of the cuvette 302 is substantially 90°. In contradistinction to the embodiment of FIGS. 3A, 3B, FIGS. 4A and 4B illustrate an embodiment 400 the corresponding transitional angle $A_T$ of which, defined by a non-zero-length $T_1$ transition between the feeder channel 302 and the bottom 312 of the cuvette, is obtuse to define a ramp-surface or wall 416, inclined with respect to the bottom surface 312. Accordingly, the transition between the feeder or inlet channel 302 and the cuvette 404 includes an entrance ramp region 406A. In one implementation, a minimum transition angle $A_T$ of about 144° between a wall in transition region and the bottom of the cuvette ensures that neither bubbles nor stagnant fluid are trapped in the corners and/or by the edges of the cuvette 404 (the upper limit for this transition angle is, understandably, 180 degrees.) Similarly, the embodiment 400 can be adapted to contain an optional exit ramp region 406B, the transition length of which is denoted $T_2$ and which has a corresponding transition angle (not shown in FIG. 4B)

It is appreciated that the smaller the microfluidic channels of the device, the more such channels are susceptible to clogging with the substance of the sample being measured. It is also appreciated that should an optimal channel size and/or dimension be chosen, such size/dimension will substantially minimize the total volume of the system.

Figure 4A:
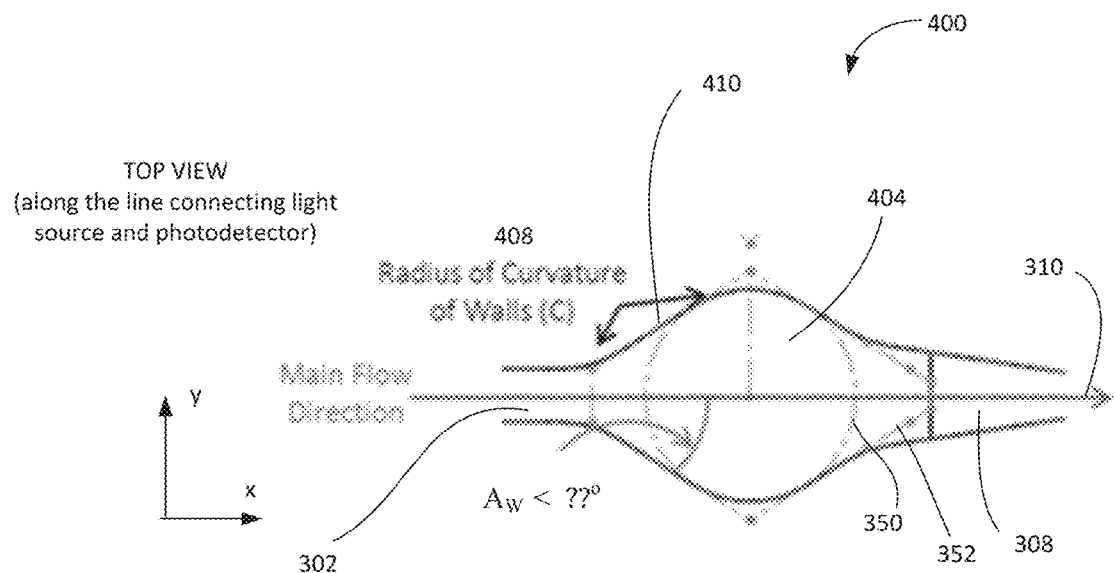
FIGS. 4A and 4B are views of an embodiment which is configured to minimize and/or eliminate formation of air-bubbles in a microfluidic cuvette.
Figure 4B:
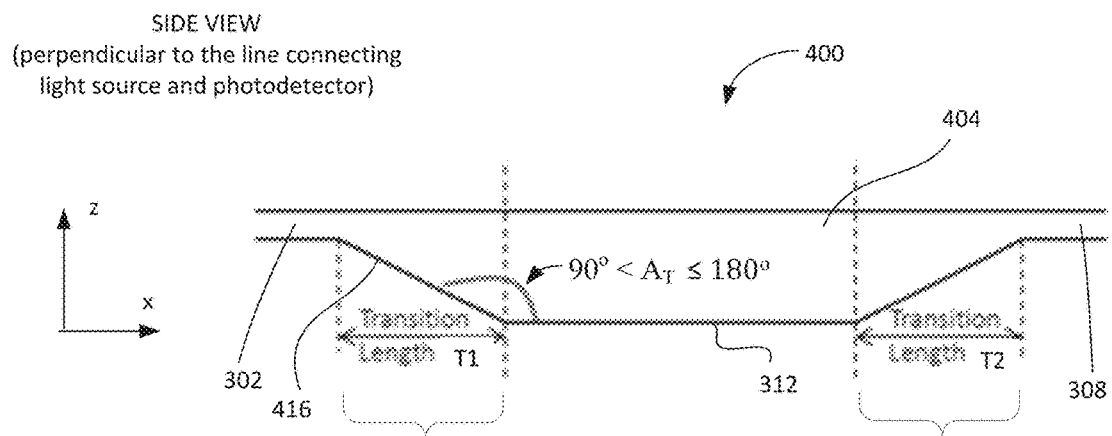

In either of FIGS. 3A and 4A, the circular dashed line 350 identified the area or footprint, of the corresponding cuvette 304, 404, that is required to ensure that all light leaving the source and reaching the detector has passed through the cuvette (and thus the sample). The dashed line 352 defines a parallelogram corresponding to tangents to fluidic cuvette walls.

According to an embodiment of the invention, the spatial rate of widening of the microfluidic network at the entrance of the cuvette, at the transition region between the inlet portion and the cuvette, is sufficiently low to ensure that the fluid sample proximate to the wall of the cuvette doesn't separate from the wall and form bubbles near the edges of the cuvette. For example, the fluid sample may be controlled using a boundary layer or surface tension effects. This spatial rate of widening of the transition portion is defined, for example, by an angle of widening $A_W$ formed by a wall in the transition region with respect to an axis of at least one of the inlet and outlet portions; the value of $A_W$ is smaller than a threshold angle value $\theta$. If, as illustrated in FIG. 3A, such angle $A_W$ between the wall 306 and the direction of the flow 310 exceeds the operationally corresponding threshold value $\theta$, the nature of interaction between the fluid stream in the separation zone 316 and the wall 306 is likely to promote formation of the bubbles 320 (region B in FIG. 3A) in the cuvette 304B. In contradistinction with the embodiment of FIGS. 3A and 3B, the embodiment of FIGS. 4A and 4B, having a cuvette 404 that is characterized by $A_W < \theta$, does not promote formation of the bubbles. In one embodiment, the value of the threshold angle $\theta$ is about 36 degrees and, therefore, $0 \leq A_W \leq 36°$. In another embodiment, the value of the threshold angle is about 30 degrees and $0 \leq A_W \leq 30°$, and in an alternative embodiment the value of the threshold angle is about 25 degrees and $0 \leq A_W \leq 25°$. In a specific case when $A_W \sim 0°$ and the depth of the feeder channel 302 approximately equals to the depth of the cuvette 304, 404 (not shown), there is substantially no potential for trapping air bubbles or leaving stagnant fluid at the bottom of the cuvette.

Furthermore, an embodiment of the IPM of the invention (such as the IPM 200 of FIG. 2, for example) is optionally equipped with a unit providing a positive air flow through the microfluidic network including the cuvettes 210, and each of the cuvettes 210 is adapted to ensure that there are no 'stagnant' areas in the cuvette in which the residue of the fluid sample remain after the cuvette has been flushed with air. Accordingly, and in further reference to FIGS. 4A, 4B, the radius 408 of curvature defined by a cuvette wall 410 in a cross-sectional plane that contains the axis 310 of fluid flow and that is substantially normal to the optical axis (locally defined as z-axis) should be maximized. In one example, where the footprint of the cuvette of about 2 mm (as defined by the dashed circle 350) implies a maximum radius of curvature of about 1 mm for the channel walls in the middle of the cuvette region (approximately at a midpoint between the inlet 302 and outlet 308 of the cuvette).

Optimization of a Multiple-Cuvette-and-Channel Multiplexed Geometry

Embodiments of the invention employ reusable microfluidic chips or elements that combine, in a spatially multiplexed fashion, multiple individual cuvettes each of which is adapted for a designated unique type of measurement. For example, multiple individual cuvettes on the same chip may be used for contemporaneous measurements of the same type of sample the concentration of which is different in different cuvettes. In a related example, multiple individual cuvettes on the same chip may be used for contemporaneous measurements of samples of different types or nature (for example, samples containing different analytes). In either case, to use the smallest possible volume of a sample in an individual cuvette, the 'dead' volume of such cuvette is minimized, as mentioned above. A person of skill in the art will appreciate that the required operational independence of the individual but structurally-multiplexed cuvettes from one another begs a question of how to preclude different sample aliquots in different individual cuvettes from mixing with one another and, by virtue of such mixing, introducing an error in the measurements. In addition to one fluid mixing with another, one should also appreciate the need to overcome filling and cleaning of individual cuvettes independently due to the varying time constraints of each assay (reaction/incubation times) with respect to sample processing logistics in a multiplexed system.

This requirement becomes even more stringent if another requirement is imposed to not remove the reusable microfluidic chip from the photometric apparatus between immediately sequential measurements.

Put differently, the complexity of these problems can be phrased as achieving the operational multiplexing of cleanable cuvettes on the same (optionally non-removable from the photometric apparatus) chip, while (i) minimizing the number of necessary fluidic connections on the chip, to reduce the overall footprint of the chip and the 'dead' volume of the cuvettes and (ii) ensuring that samples in individual cuvettes are substantially isolated from one another. According to an embodiment of the invention, a solution to this complex of problems is provided by merging the individual outlet channels of individual cuvettes into a common outlet for the overall multiplexed system of cuvettes. The following discussion is provided in reference to FIG. 5 providing a diagram of an embodiment 500 of a multiplexed microfluidic chip for use with an embodiment of the photometric apparatus of the invention.

Sample Isolation.

The embodiment 500 shows an example of multiplexing of individual microfluidic elements each of which includes a corresponding input channel or inlet 502(a, b, c, d, e, f, g, h, i, j), a cuvette 504(a, b, c, d, e, f, g, h, i, j), and a corresponding individual output or outlet 508(a, b, c, d, e, f, g, h, i, j). For simplicity of illustration, only some of the above-mentioned elements are labeled in FIG. 5. The individual inlets 502a through 502j serve a purpose of operational isolation of individual cuvettes 504a through 504j so that different samples in these cuvettes do not contaminate one another. For simplicity of the fluidic manifold that will distribute and return samples, the individual outlets 508a through 508j are merged to and share a common chip outlet 516. To operationally isolate the samples in the cuvettes 504a through 504j, the fluidic resistance of the individual cuvette outlets 508a through 508j must be sufficient to ensure that pressurized fluid in the main outlet channel 516 flows out of the device (along the arrow 518) through the common outlet rather than back, up-the-stream through another cuvette (for example, through the outlet 508a towards the cuvette 504a). The fluidic path length corresponding to an individual outlet channel 508a through 508j must be sufficiently long to prevent diffusive mixing of the samples in individual cuvettes 504a through 504j.

Figure 5:
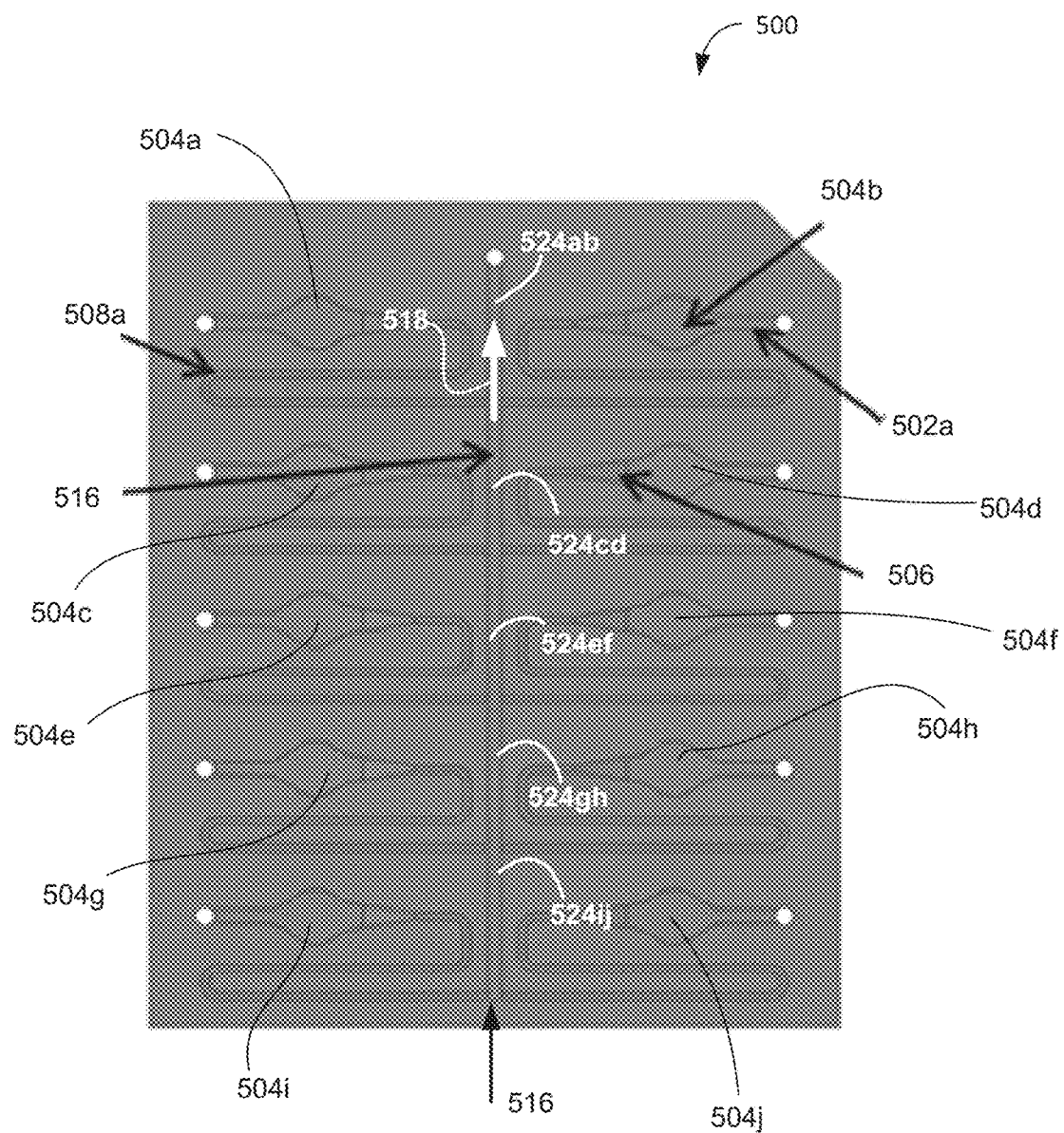
FIG. 5 is a diagram illustrating schematically an embodiment of a multiplexed fluidic network containing multiple cuvettes (each cuvette having corresponding inlets, high-resistance outlets) and a low-resistance main outlet channel.
Figure 6B:
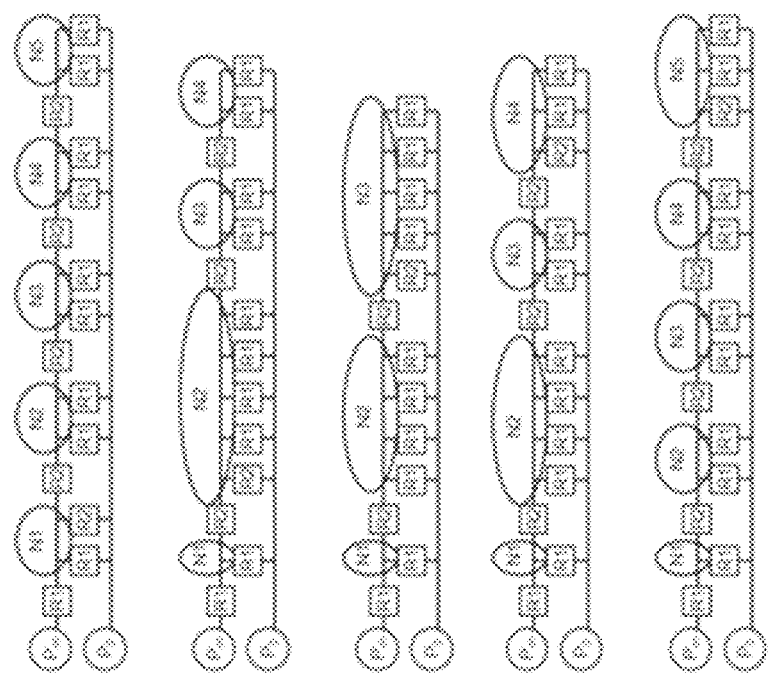
FIGS. 6A and 6B are diagrams illustrating the fluidic model representing the microfluidic network embodiment of FIG. 5.
Figure 6A:
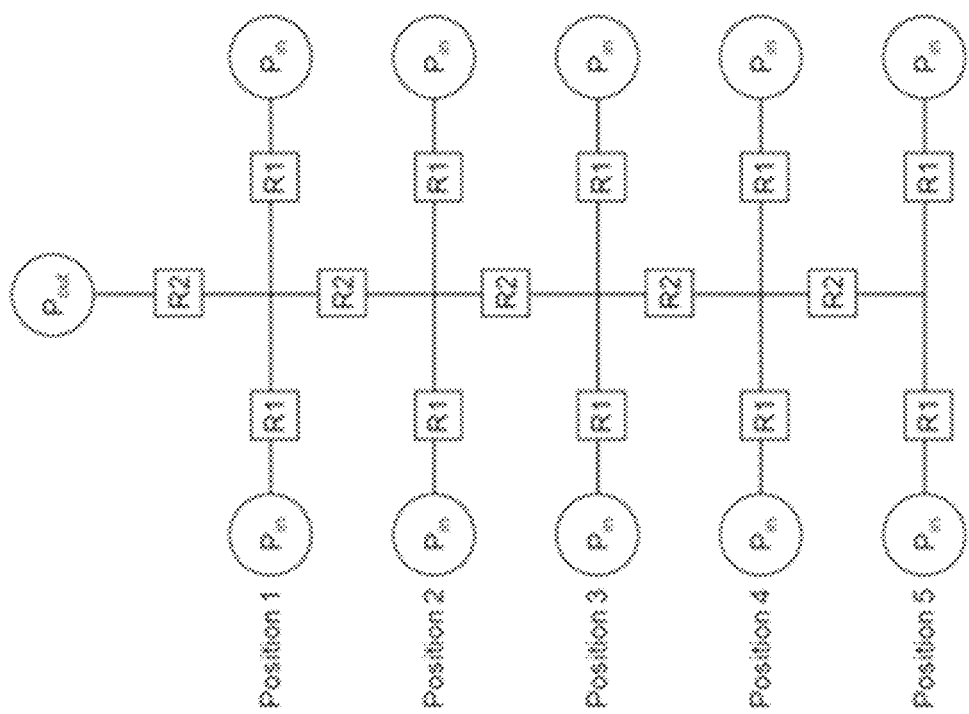

In reference to FIGS. 6A and 6B, showing examples of two schemes describing the fluidic model of the embodiment 500 of FIG. 5, the fluidic resistance R1 of the individual outlets 508a through 508j is, in one implementation, approximately 2 to 3 orders of magnitude higher than the resistance values R2 of segments 524ab, 524cd, 524ef, 524gh, and 524ij, of the main outlet channel 516, that are located between the cuvette pairs (504a, 504b), (504c, 504d), (504e, 504f), (504g, 504h), and (504i, 504j), respectively. In one implementation, the ratio of the resistance values R1/R2 is about a number of the individual cuvettes in the embodiment or higher. In different implementations, the ratio of resistance values R1 and R2 may range between about 200 and about 10,000. Furthermore, the entire measurement system, which includes the embodiment 500, is preferably a closed system with no air in any line in order to prevent residual flows. If there is any air in the system, it will compress during pressurization of the system and then when the system is de-pressurized, the air will expand causing residual flows which can lead to sample contamination. The nodes $N_i$ within the system of FIG. 6B represent the locations at which the fluidic pressure is approximately the same.

EXAMPLES

Figure 7:
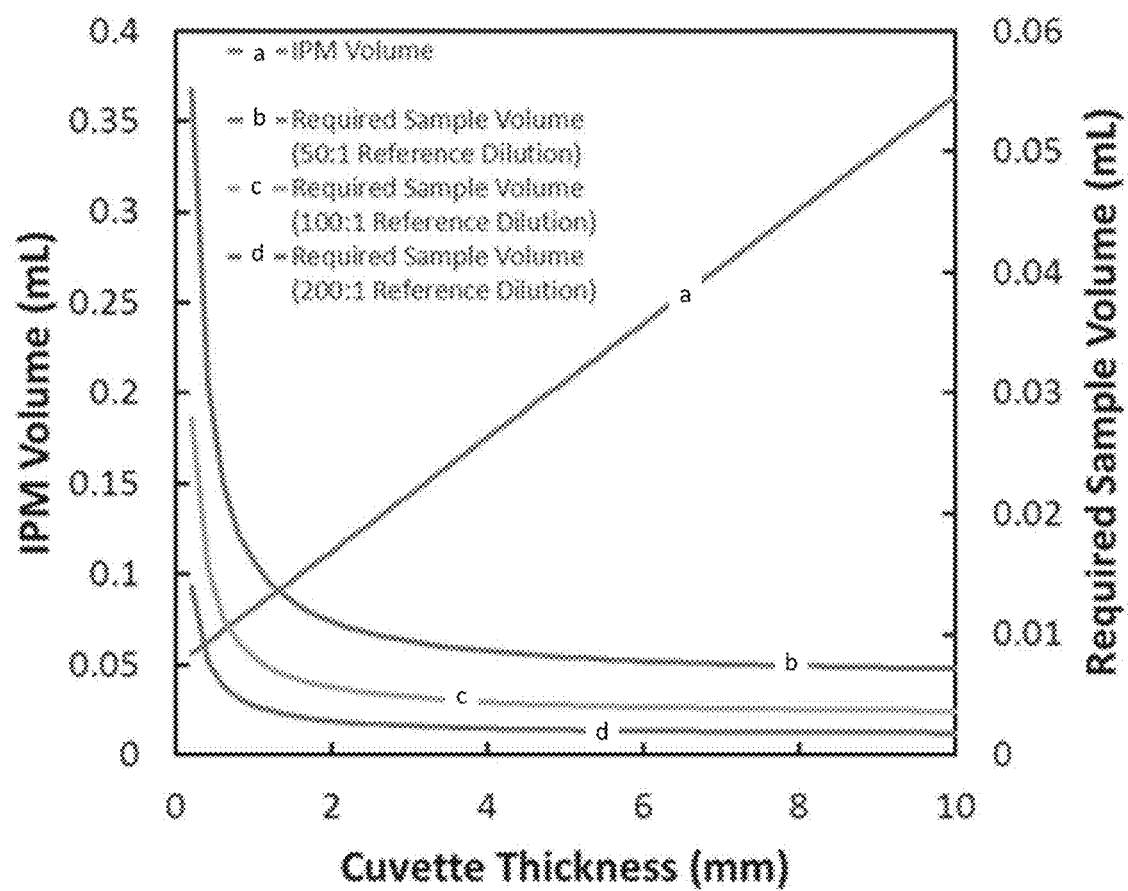
FIG. 7 is a plot showing how the volume of the integrated photometry module (IPM) and the required volume $V_S$ of the undiluted sample depend from a thickness of a cuvette, for several values of dilution ratio D.

In one implementation, and in further reference to FIGS. 2, 4A, 4B, and 5, an individual cuvette in a multiplexed chip 212, 500 used in the IPM 200 has a footprint defined by a circle with a diameter of about 2 mm. FIG. 7 is a plot showing a volume of the required undiluted sample as a function of the cuvette thickness and the reference dilution ratio, according to Eq. (8). According to FIG. 7, a cuvette with thickness of about 1 mm optimizes the reduction of the 'dead' volume of the overall microfluidic component system while maintaining, at the same time, an undiluted sample volume below about 0.02 mL. Therefore, FIG. 7 provides an illustration to an embodiment in which the operation of the multiplexed microfluidic chip 212, 500 is optimized for the cuvettes having thickness of about 1 mm. In the example of FIG. 7, the entrance channels (302, 502a through 502j of the cuvettes (404, 504a through 504j) each have a depth of about 1 mm and a width of about 0.5 mm. The transition angle $A_T$ corresponding to the individual inlet transition area 406A is chosen to be about 180°, as discussed in reference to FIG. 4B. Each of the individual inlets (302, 502a through 502j) expands into the corresponding cuvette (404, 504a through 504j) at an angle $A_W$ of about 32°, as discussed in reference to FIG. 4A. The walls of an individual cuvette have a curvature radius 408 of about 1 mm. The individual exit channels (308, 508a through 508j) have a width of about 0.25 mm, a depth of about 0.05 mm, and a length of about 26 mm. The transition region 406B from an individual cuvette area to the corresponding exit channels (308, 508a through 508j) has a length $T_2$ of about 1.9 mm. The transition angle $A_T$ corresponding to the outlet transition region 406B is chosen to be about 153°. The main outlet channel 516 has a depth of about 0.25 mm and a width of about 0.5 mm. The distance between pairs of individual outlet channels along the length of the main outlet channel is about 5.4 mm.

In one implementation, and referring again to FIG. 2, the IPM 200 is operated as follows. The entire system is heated to approximately 37° C. (for example, for about 5 minutes) until a steady state is reached. Once the temperature of the system is stabilized, a dark reference voltage is measured for each detector 244 by determining the voltage corresponding to each detector when the respectively corresponding LED 254 is turned off. The IPM 200 is initially empty (contains air) prior to any measurement. Blank solutions are pre-loaded into a sample manifold (not shown in FIG. 2). The manifold is connected to the plastic cuvette with 3"-6" long rigid tubing (such as, for example, the one by PEEK, 1/32" OD, 0.015" ID) followed by 3"-6" long flexible tubing (such as that of Tygon, 0.06" OD, 0.02" ID). The manifold is pressurized to about 1 bar and the blank solutions flow into their respective cuvettes. The flow is stopped by venting the manifold to atmospheric pressure when liquid begins to flow out of the outlet tube (in one example, in about 5 to 15 seconds). The system is then closed by clamping the flexible tubing to ensure that there are no air pockets in the system (such as the head space in the manifold).

The transmission of light through the blank solution in a single cuvette is measured by turning on the LED 254, corresponding for that cuvette, waiting for a short period of time (such as 5 ms, for example), recording the voltage of the photodetector 244, turning off the LED 254, and waiting for another period of time (for example, 200 ms). This process is repeated three times and the average detector voltage for that cuvette is determined. The dark reference voltage for that detector is subtracted from the average voltage and the result is recorded. The process is repeated for each of the ten cuvettes in series.

Once the blank solutions have been measured, the sample vials are removed from the manifold and tubing is unclamped. The manifold is again pressurized to 1 bar and the system is flushed with air until all of the liquid is removed (for about 5 to 15 seconds). The samples are then loaded into the manifold in the same manner as the blank solutions.

The transmission of light through the samples is measured in the same manner as for the blank solutions. The absorbance of the samples is determined by calculating the logarithm of the ratio of the transmittance value corresponding to the blank solution to the transmittance value of the sample (corrected with the dark reference value, as already described).

For endpoint reactions, three measurements are taken for each sample and the averaged absorbance value is used to calculate the sample concentration. For rate reactions, the absorbance of the sample is continuously monitored (the system cycles through all of the cuvettes until stopped) and the rate of change of absorbance is used to determine the sample concentration.

The IPM embodiment 200 of FIG. 2, structured as described above in reference of FIG. 7, requires at least 0.02 mL of the fluid sample (for example, blood, serum, saliva diluted with reagent and/or buffer) to operate. In order to make accurate measurements of sample absorbance, the liquid sample in any given cuvette must not be contaminated by other samples. This means there can be no residual flows in the system. The tube clamping described in the previous section takes care of this requirement.

For enzymatic rate reactions, the sample and reagent are mixed outside the system at a temperature significantly lower than the chose steady-state temperature of operation (which, in the provided example, is about 37 C) in order to suppress the enzymatic rate reaction. When the sample is flown into the cuvette, it is warmed to 37 C as quickly as possible in order to make an accurate constant rate measurement. Assay chemistries for this system should preferably be adapted to be compatible with that process workflow.

In order to make accurate sample measurements, the LEDS 254 and corresponding electronic circuitry are configured to ensure that the output LED intensity does not drift over time. In particular, the duty cycles (on time/cycle time) of the operation of the LEDs 254 are chosen to be low enough to ensure that the LED intensity doesn't drift. In one example, the reported operation of '5 ms on/200 ms off' satisfies this requirement for all of the LEDs currently used in the IPM system 200.

As was already alluded to above, one of the problems persistently accompanying the operation of a microfluidic photometry module during the measurement is a drift (or spatial shift, or repositioning) of a fluidic sample housed in a volume through which light, used for measurement, is passed between the source of light and the optical detector (such as a cuvette portion of the microfluidic channel). While one might expect that, under some circumstances (and depending on assay chemistry), capillary forces would help maintaining the volume of the fluidic sample firmly in place, the fact that at least one of the front and back ends or interfaces of the fluidic sample in the channel is conventionally left in its natural state (or free, or unattended) allows for minute movements of the sample caused by any disturbance occurring in the ambient media surrounding the sample during the measurement. Alternatively or in addition, minute movements of the sample filling the cuvette may also be caused by differences in pressure levels on opposite sides of the sample (up- and downstream with respect to the cuvette). Such movements or drift occurs at amplitudes practically sufficient to perturb the measurement and cause such uncertainty of the results that often shed a doubt on accuracy and/or repeatability of the measurement.

It would be appreciated from further disclosure, that implementation of the embodiments of the invention increases the quality and reliability of photometric, fluorometric (for example, chemiluminescent), and turbidimetric analyses of sample to determine concentration of analyte(s) (in a non-limiting example—for in vitro diagnostic to determine concentrations of specific analytes in a blood sample). Specifically, embodiments of the invention advantageously improve the quality of multiple photometric and/or turbidimetric and/or fluorometric (for example, chemiluminescent) measurements that have to be performed in the same cuvette of the same chosen channel of the channel network, requiring the system to have both inlet and outlet portions of the channel so that multiple samples can be allowed to flow through. Two examples of such a requirement are: 1) a situation when the cuvette is reused for testing of multiple samples; and 2) when a calibrant is measured in the same cuvette prior to measuring the sample of interest. It has been observed, in practice, that flow through the cuvette(s) is susceptible to residual flow created by differences in pressure upstream and/or downstream of the cuvette and/or capillary forces, and that this residual flow detrimentally affects the analysis of the sample. The observed effect is of particular importance in the case of assays that have to be maintained at a specific temperature (and/or within a specific temperature range) within the cuvette—such as is the case, for example, with enzyme catalyzed reactions. Furthermore, in case when multiplexed configurations of microfluidic channels are employed that connect, downstream, to a common waste collection reservoir (storage volume), it may be required to temporarily isolate one portion of the overall system from another to prevent the fluidic pressure in one of the channels from influencing the fluid flow in other channels. Notably, in some cases, in the same network of channels, it may be important to ensure that any combination of analyses (photometry, turbidity, chemiluminescence) can be performed simultaneously.

Figure 8:
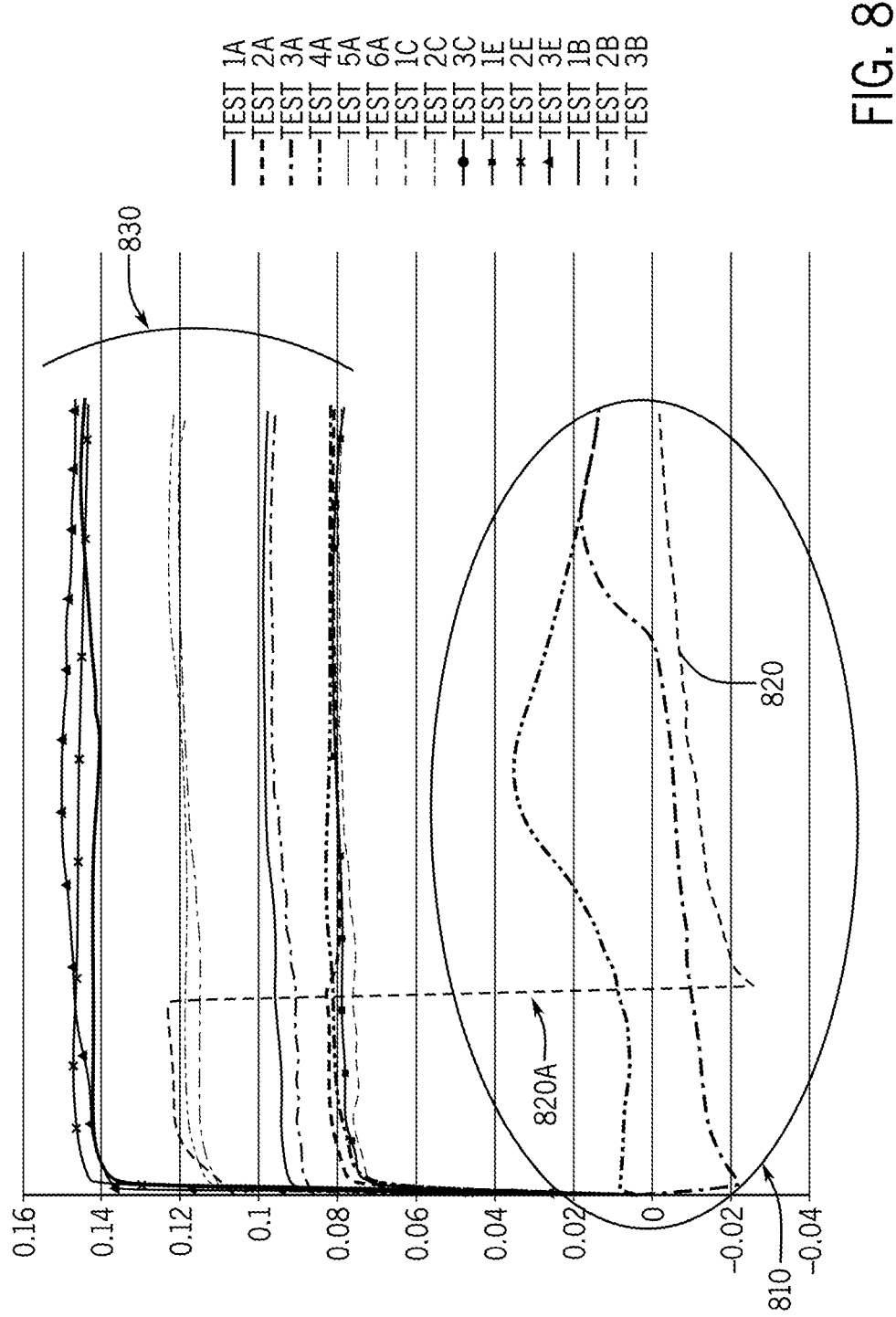
FIG. 8 provides empirically-obtained data evidencing the persisting signal drift and associated uncertainty of acquired data that accompanies measurements performed with microfluidic photometric systems in which a fluidic sample is not spatially locked and immobilized with respect to the housing volume containing such sample, as well as comparison with data similarly-acquired with the use of an embodiment of the microfluidic photometric system configured to prevent a possibility of fluidic sample movements during the measurement.

Empirically-procured evidence of such seemingly-insignificant problem is provided by FIG. 8, where the photometrically-acquired optical data representing absorbance of the sample ("absorbance units") are plotted as a function of time. The plots presented in this Figure illustrate two situations: the one often occurring during the conventionally-configured photometric measurement (that is, without a precaution of "locking" the sample in place), and the other corresponding to the implementation carried out according to the idea of the invention (that is, with the fluidic sample "locked" in its position to avoid the drift caused by external disturbances and/or changes of environment, as will be discussed in detail below). The first situation is represented by the group 810 experimental curves, each of which exhibits a sharp transition such as transition 820A of the curve 820, during which the fluidic sample being measured experiences a minute spatial drift disturbing and changing the reading at the optical detector. The second situation is represented by the group 830 of the curves, each of which exhibits a clearly monotonic, differentiable behavior. As will be readily appreciated by a skilled artisan from the discussion below, the drastic change in reliability of the measurement is caused by the implementation of the idea of the invention.

Considering the miniscule amounts/volumes of fluidic samples that the described above embodiments of the invention are capable of measuring, such drifts or shifts (see transition 820A of curve 820) present a problem that begs a reliable solution. According to the idea of the invention, the fluidic sample—once positioned in a cuvette in a fashion appropriate for photometric measurement—is spatially locked or fixed or immobilized in its position by intentionally preventing a possibility of either of its front or back interfaces to move. This is achieved by using a fluidic valve at an identified point on one side of the sample to prevent the sample from moving pass such identified point and to isolate the downstream compressive fluid (gas, liquid) from the sample during the measurement. In a related embodiment, this achieved by using a fluidic valve at an identified point on one side of the sample to prevent the sample from moving past such identified point while, at the same time, applying a fluidic pressure to the other, remaining end/interface of the sample. The latter can be carried out with, for example, a flow of gas passed through a given channel of the network of the microfluidic channels in the direction of propagation of the fluid-sample-being-measured through the system, in a related embodiment, however, the system may be appropriately configured to employ a flow of liquid.

A person of skill in the art will readily appreciate that the components and/or elements of the system and the overall system itself generally can be and are intended to be implemented not necessarily in a single, common for all components/elements structural layer of the system. In one example, multiple microfluidic channels of the overall network of channels may be disposed in a single substrate (and even in a single plane of such substrate), such as in the case already discussed in reference to FIG. 5, for example. In a related case, however, as discussed below, the operability and efficiency—as well as cost—of the overall system are increased by purposefully and intentionally extending different elements of the system (such as different portions of the microfluidic network) into and/or through multiple substrates and/or planes—often transverse to one another and generally made of different materials—in a fashion that allows for substantial minimization of a footprint of a given microfluidic chip.

Outlets of individual, constituent channels of the network of microfluidic channels of the system (such as an outlet portion of the channel, through which the already-measured fluidic sample is propagated from the cuvette) may be structured to lead to a main outlet channel (contained within the same chip carrying the network of channels and shared by multiple individual constituent channels, by analogy with the structure illustrated in FIGS. 5, 6A). The system may be further configured such as to direct the main outlet channel to a storage volume collecting used i measured fluidic samples. Alternatively or in addition, such storage volume can be formed in direct contact (be permanently integrated) with the chip containing the network of channels (for example, be formed on a substrate already carrying at least a portion of the network of channels). In a related embodiment, however, the storage volume—if present—is formed on an independent piece of material that is not inseparably integrated with a portion of the microfluidic network but, to the contrary, is disposed on a hardware component that can be removed from the system on its own (to be disposed of, for example).

Figure 9:
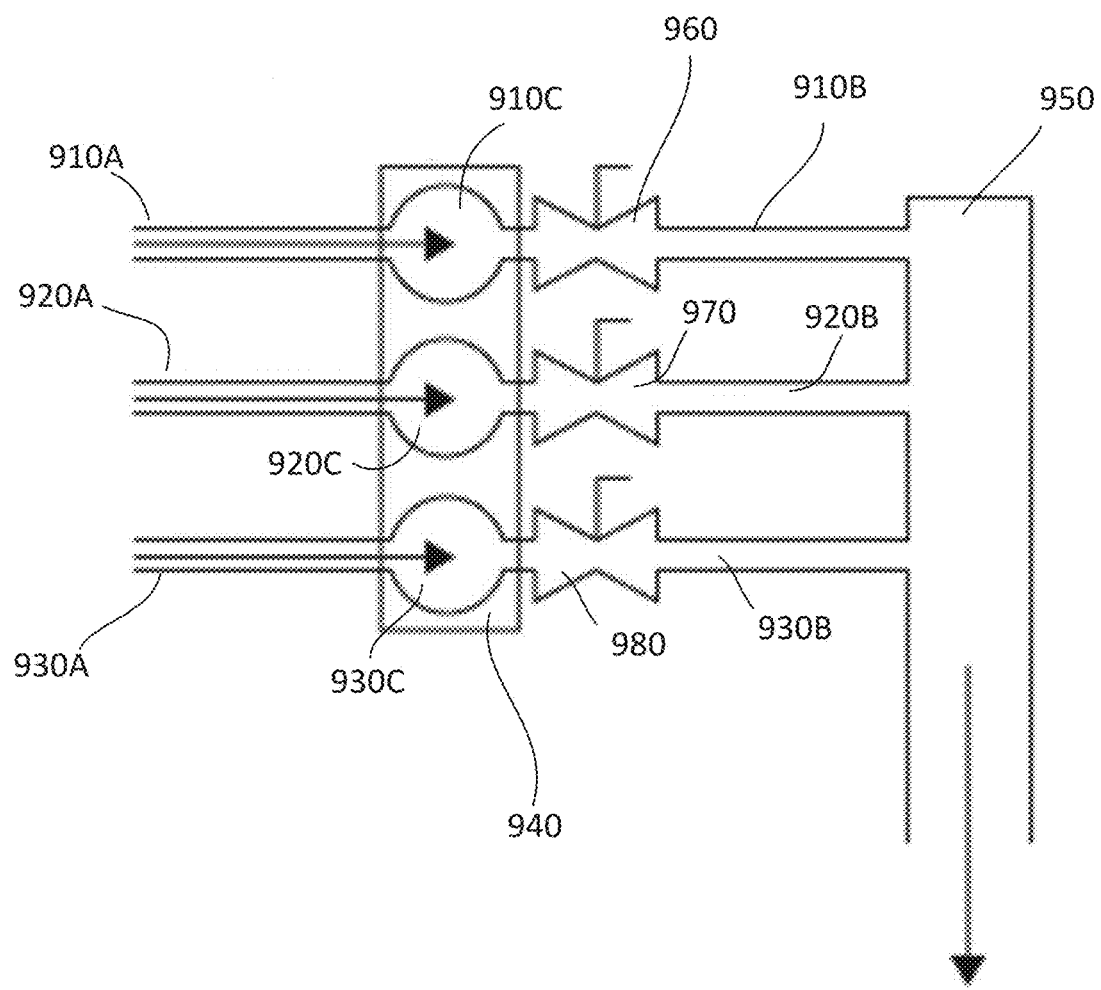
FIG. 9 schematically illustrates a concept according to which the fluidic circuitry of an embodiment of the invention is configured.

Putting aside, for a moment, the specific description of how the components of the network of microfluidic channels are oriented with respect to one another, the concept of locking the fluidic sample in place to avoid a drift of the sample during the measurement can be illustrated with the schematic of FIG. 9. Here, a plurality of constituent channels 910, 920, 930 are shown, each having a corresponding inlet portion 910A, 920A, 930A and a corresponding outlet portion 910B, 920B, 930B, with a corresponding cuvette portion 910C, 920C, 930C in between. In this example, the cuvette portions 910C, 9200, 930C are shown to be formed on a dedicated substrate 940 (which may or may not be the same substrate that carries at least one of the inlet and outlet portions, too). The outlet portions 910B, 920B, 930B are shown to lead to an area 950 (which, depending on the specific implementation may be a main outlet channel leading, in turn, to the storage volume, or a storage volume itself). Arrows in FIG. 9 indicate a direction of flow of fluidic sample(s) through corresponding channel(s) during the operation of the photometric system of the invention. As schematically shown, fluidic valves 960, 970, 980 are used on one side of channel(s)—shown, in FIG. 8, downstream from the cuvettes 910C, 920C, 930C—to reversibly block path(s) for sample(s) moving along the channel(s). Once the movement of a given fluidic sample down a given channel is stopped by closing a corresponding valve, the locking of the sample in place is further effectuated by pressuring the channel at the other side with respect to the corresponding cuvette.

Figure 10A:
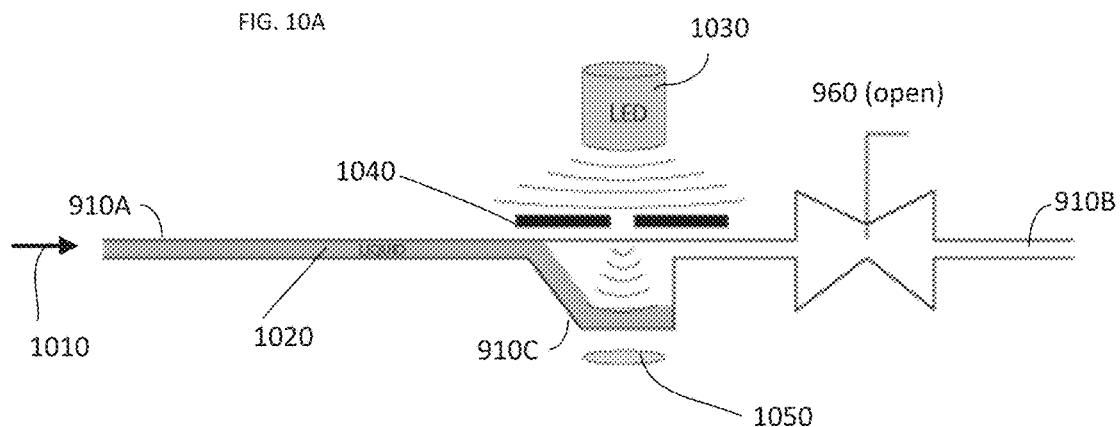
FIGS. 10A, 10B are schematic diagrams showing steps of preparing a fluidic sample for photometric measurement, according to the idea of the invention.
Figure 10B:
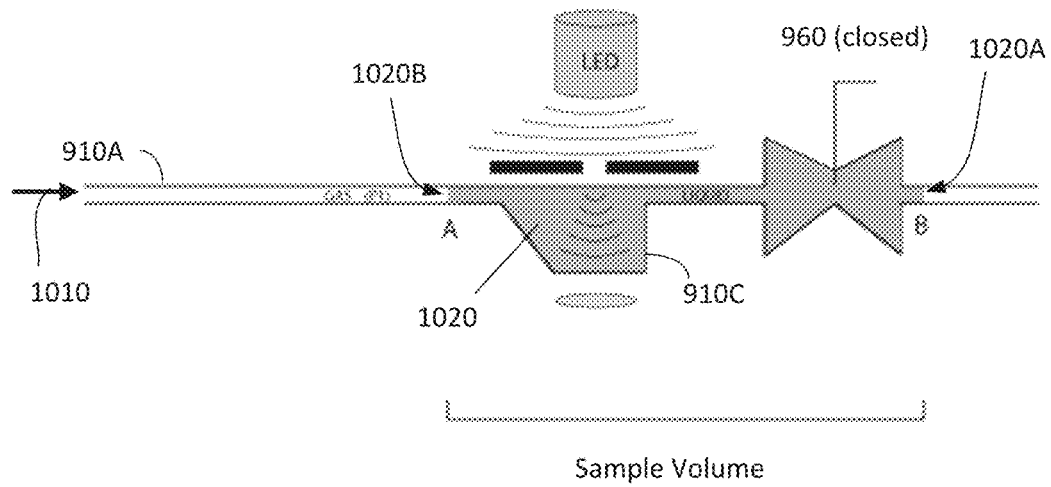

The principle of preparation of a given microfluidic channel for a photometric measurement of the fluidic sample contained therein, arranged according to an embodiment of the invention, is further illustrated in reference to FIGS. 10A and 10B. Here, for simplicity of illustration, only one of the channels of FIG. 9 is considered and shown in side view. With the downstream valve 960 open, fluid (for example, gas) pressure 1010 is applied to the back, tailing interface of the fluidic sample 1020 in the inlet 910A to force the sample 1020 through the cuvette 910C and the valve 960. The fluidic pressure can be formed with the use of, for example, a pump that is appropriately connected to the inlet 910A upstream with respect to the cuvette 910C. Prior to taking the analytical measurement, the photometric system (some of principal components of which are shown here as a light source 1030, and optical aperture 1040, and an optical detector 1050) is used to detect the progress of the front interface of the fluidic sample 1020 towards the valve 960. Referring now to FIG. 10B, once the front end 1020A of the fluidic sample 1020, pushed from the back with the pressure front 1010, passes through the valve 960, the valve is shut to prevent any further forward drift/repositioning of the sample 1020 while, at the sample time, the fluidic pressure 1010 applied to the back end 1020B of the sample 1020 is maintained to prevent the repositioning of the end/tail interface of the sample 1020 on the other side of the cuvette 910C. The volume of a sample contained, under such conditions, between the interfaces 1020A, 1020B defines the sample volume used for a photometric measurement; it is preferred to dimension the channel and/or valve and/or pressure applied to the tailing interface of the sample in such a fashion as to minimize this volume. One guideline for minimization of the sample volume may be to minimize the distance between the valve and the cuvette portion of the channel.

Referring again to FIG. 10B, several modalities can be used for real-time determination of the position of the fluid front interface 1020A of the sample 1020 downstream of the valve 960, according to an embodiment of the invention. For example, the front 1020A can be localized with the use of optical detection (based on absorption, refraction, or scatter of light, directed to a point downstream of the valve and the use of an external optical detection unit). Alternatively or in addition, the propagation and/or location of the front 1020A pass the valve 960 can be determined with the use of electrical detection by measuring the impedance value, for example. Alternatively or in addition, the mechanical methods can be used as well such as the determination of pressure with the transducer-containing module in operable communication with a portion of the microfluidic channel and/or employ of a limit-switch, as may be known in the art. The use of predetermined parameters of process variable (such as fluidic pressure 1010 and time) is further made to drive the sample 1020 beyond the valve after the feedback signal is detected by the appropriate sub-system of the photometric system.

Figure 11:
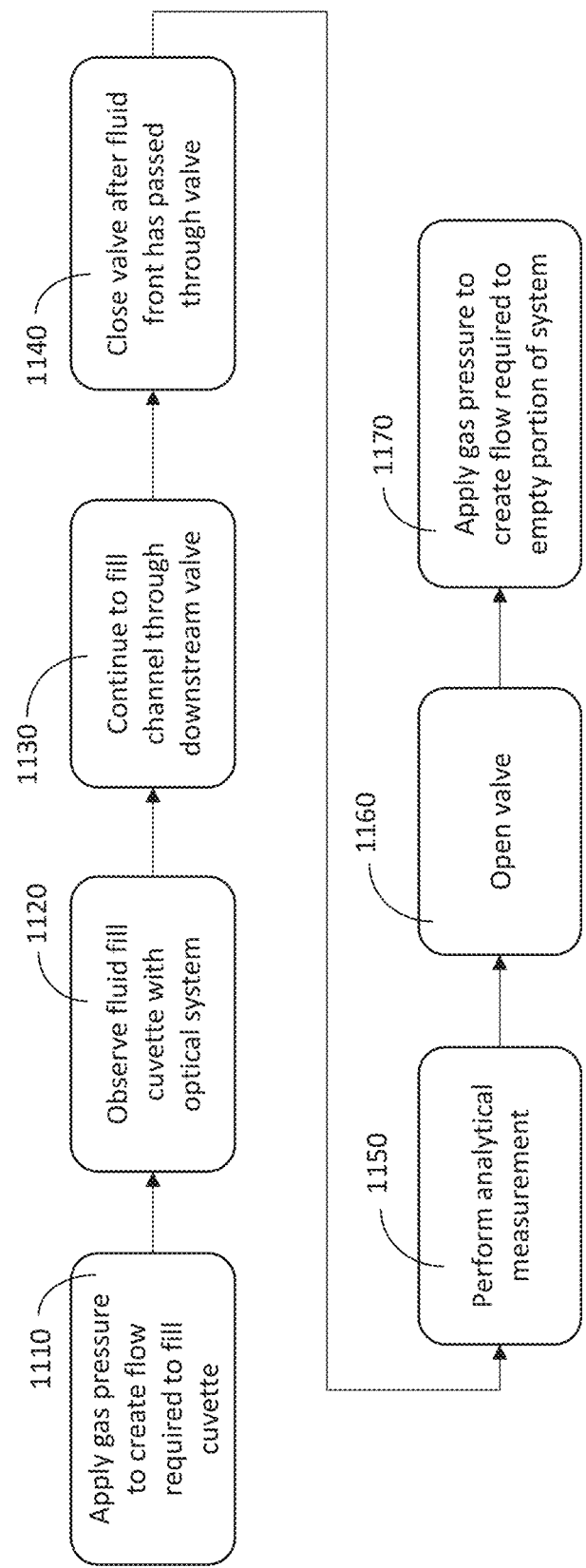
FIG. 11 is a flow-chart representing an embodiment of the method of the invention.

FIG. 11 contains a schematic chart representing some of the steps of a method of the invention. A person of skill will appreciate that an embodiment of the method contains at least some of the following processing elements. At step 1110, fluidic pressure is applied to the tailing end of the fluidic sample in a channel to move the sample towards the cuvette. At 1120 (and in further reference to FIG. 10A), the optical system of the photometric module is used to observe the filling of the cuvette with the fluidic sample and/or to confirm that that cuvette has been filled without the formation of air-bubble within the cuvette. The continually-applied to the tail interface of the sample pressure is then used to move a portion of the spatially-continuous sample pass the cuvette through the downstream valve, 1130. Once the front interface of the sample is observed to have moved pass the valve, the valve is closed at 1140 to ensure that the sample can no longer move in the forward direction while, at the same time, the tailing interface of the sample is maintained under the fluidic pressure directed downstream to prevent the sample from moving backward and to avoid a spatial drift or repositioning of the sample due to a change of ambient conditions. (In a related implementation, however, it may be possible to remove the upstream pressure of the system once the downstream valve is closed, while preventing the backflow of the fluid. It may be preferred to retain the stored energy of the upstream pressure for efficiency of operation of the overall system).

The so-fixed-in-place fluidic sample is then subjected to the photometric measurement at 1150 to determine sought-after parameter(s) as discussed above. Upon the conclusion of the analytical measurement, the valve is opened at 1160 to allow for the forward movement of the sample out of the cuvette and pass the valve under the fluidic pressure applied to the tailing end of the sample. During the ridding 1170 of the portion of the channel (e.g., cuvette) of the fluidic sample, the parameters of the fluidic pressure applied to the tailing end of the sample may be judiciously modified to ensure that such channel portion is completely emptied.

The process of handling a fluidic sample upon its propagation through the network of microfluidic channels and photometric measurement of analyte(s) contained in the sample can be effectuated with the use of several embodiments of the microfluidic chip carrying such network. The valve(s) of the embodiments may be generally arranged as external valve(s) (that is, arranged externally to the overall. Whole network of channels such as to control the fluid flow through a main outlet channel that is common to or shared by individual outlet portions of constituent channels of the network). Alternatively, the valve(s) can be arranged as internal valve(s) (that is, valve(s) governing the fluidic flow through outlet portions of individual constituent channels of the network. Further below, three related non-limiting examples of so configured embodiments are discussed in reference to FIGS. 12; 13A and 13B; and 14A, 14B, 14C, which present implementations in which the channels of the network are configured to penetrate multiple structural levels and are not necessarily belong to a single carrying level or substrate.

Figure 12:
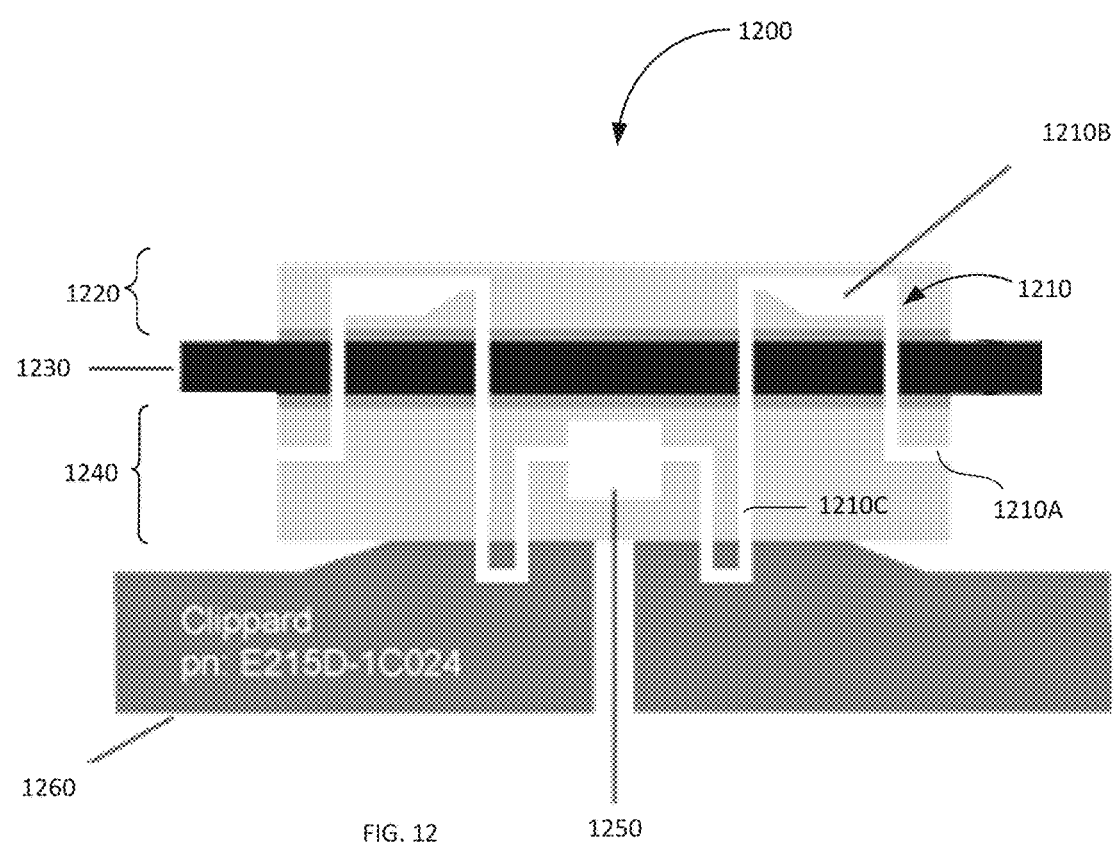
FIG. 12 provides a schematic illustration of an embodiment of a multiplexed photometer system employing external valving.

FIG. 12 schematically illustrates, in a side cutaway view, an embodiment 1200 of the microfluidic chip in which an individual channel 1210 (that includes the inlet portion 1210A, the cuvette portion 1210B, and the outlet portion 1210C) is structured to pass through at least three structural layers 1220, 1230, and 1240, operationally integrated one on top of another for proper photometric measurement. (The side view of the embodiment 1200 shows two channels 1210 configured on the right-hand side of the chip as shown and the other channel disposed substantially symmetrically with respect to the channel 1210). In particular, the cuvette portion 1210B is formed in the upper (as illustrated) layer 1220, defining a fluidic photometry module through which light is transmitted during the photometric measurement and that is carried on a mounting surface of the substrate 1230. The inlet portion 1210A leading to the cuvette 1210B, on the other hand, is directed to penetrate through the fluidic manifold layer 1240 (in directions parallel and/or transverse to a mounting surface of the layer 1240), the substrate 1230 connected to the mounting surfaces of the layers 1220, 1230, and at least in part through the layer 1220 where it merges to the cuvette 1210B. Similarly, the outlet portion 1210O of the channel 1210 emerges from the cuvette 1210B to penetrate through the photometry module layer 1220, the mounting substrate 1230, and the fluidic manifold layer 1240 on its way to the main outlet channel (main outlet) 1250 that, in this embodiment, is common to and shared by multiple constituent fluidic channels. Before merging to the main outlet 1250, the outlet portion 1210C is fluidically engaged with the external valve 1260, which is configured to block the fluid flow through the outlet portion 1210C when closed, as discussed above. (A Clippard valve can be used for this purpose in one case, as illustrated.) During the operable integration of the layers 1220, 1230, 1240, surface sealing layers such as gasket(s) and/or O-rings can be installed between the facing-each-other surfaces of these layers to provide for appropriate fluidic seals.

Figure 13A:
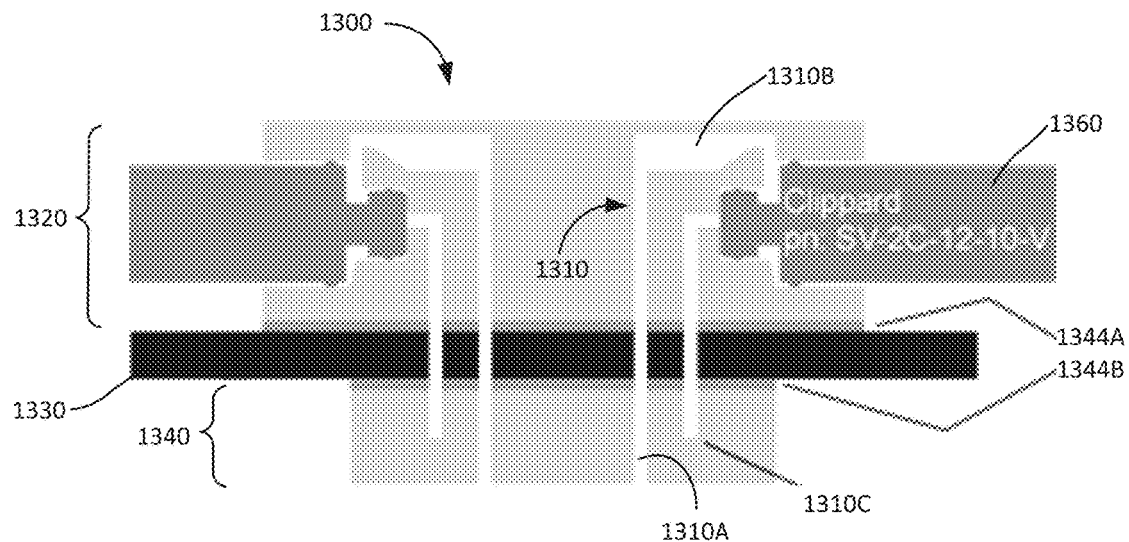
FIGS. 13A and 13B schematically illustrate an embodiment of a multiplexed photometer system with internal valving, that has the only, single outlet in a fluidic manifold portion of the system.
Figure 13B:
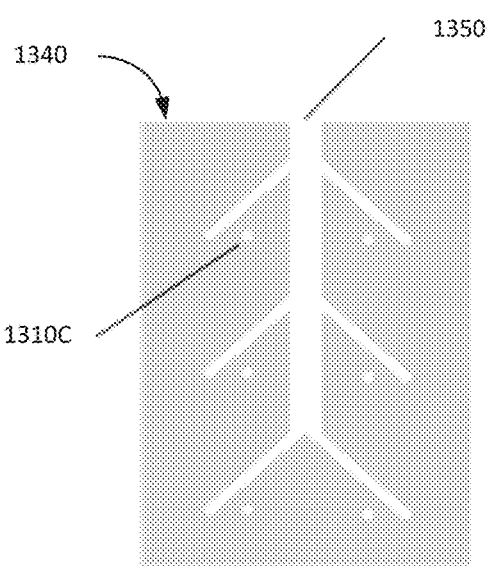

FIGS. 13A and 13B provide schematics of a related embodiment 1300. As shown, a constituent channel 1310 includes an inlet portion 1310A, a cuvette portion 1310B and an outlet portion 1310C, each of these portions of the channel 1310 formed in at least one of the structural layers 1320, 1330, and 1340 that are (optionally, reversibly) integrated with one another through the sealing layers 1344A, 1344B (such as gaskets, for example). Here, each constituent channel is complemented with a respectively-corresponding valve (as shown, the channel 1310 is cooperated with the valve 1360), which is configured in the fluidic photometry module or layer 1320. FIG. 13B schematically illustrates a top view of the fluidic manifold structural layer 1340 of the chip 1300, with the main, shared by the constituent channels outlet 1350 (optionally leading to a fluid storage volume, not shown).

FIGS. 14A, 14B, and 14C illustrate an embodiment 1400 structured by analogy with those of FIGS. 12, 13A, but exhibiting a single, shared by individual outlet portions of the constituent channels, main outlet (outlet port) 1450 that is located at least in part in the photometry module layer 1420. Here, an individual channel 1410 includes, as before, the inlet portion 1410A disposed across the structural layers 1420, 1430 (which is a mounting substrate), and 1440 (which is a fluidic manifold). In a fashion similar to those of the embodiments 1200, 1300, the structural layers 1420 and 1440 are shown mounted on the substrate 1430 with preferably interdisposed surface sealing layers 1444A, 1444B that ensure lack of leakage of the fluidic sample(s) flowing through constituent channels of the network of the chip 1400. The individual channel 1410 also include the cuvette 1410B (carried in the photometry module layer 1420), and the outlet portion 1410C passing through at least the layer 1420. The outlet portion of each of the individual channel of the network of channels is operably cooperated with a respectively-corresponding valve (one shown as 1460) that fits into a judiciously dimensioned valve port (shown as 1460A) configured in the layer 1420. FIG. 14A schematically illustrates a top view of the structural layer 1420 of the embodiment 1400, while FIG. 14C outlines the top view of the fluidic manifold layer 1440.

Each of the embodiments 1200, 1300, and 1400 is illustrated to contain multiple individual channels sharing the main outlet (optionally fluidly connected with a disposable external storage volume; not shown). It is understood, however, that a related implementation (not shown) can be structured to ensure that individual outlet portions of at least some of the constituent channels of the microfluidic network chip are directing the flow of corresponding fluidic sample(s) directly to the external storage volume and not to the shared main outlet channel portion.

The operation of any of the embodiments of FIGS. 12, 13A, 14A according to the general principle outlined in connection with FIG. 11 produced an empirical result already summarized in FIG. 8. Data presented in FIG. 8 evidence the reduction and/or elimination of spatial drift of the fluidic sample(s) by temporarily and reversibly bringing the fluidic sample(s) to a standstill (that is, stopping and/or restraining and/or spatially stabilizing the sample(s)) with no air present within the boundaries of the sample(s) for the duration of a photometric measurement as a result of causing the sample(s) in fluidic channel(s) to interact with pressure forces simultaneously applied to opposite ends of such sample(s) by respectively-corresponding fluidic valve(s) and auxiliary fluid(s) such as gas. As a result of the implemented solution, the persisting problems caused to the photometric measurement in embodiments of related art—that is, the presence of large modulations of measured intensity values below and/or above the floor of the measurement, leading to uncertainties of how and where to average acquired data to obtain physically-correct results—was solved. As evidenced by FIG. 8, as a result of implementing an embodiment of the invention not only the abrupt (see curve portion 820A) but also a continual-in-time drift (see curve portion 840) of the fluidic sample is substantially eliminated, leading to increased accuracy and precision of the now-reliable analytical measurement(s). A skilled artisan will readily appreciate that, when a specific embodiment of the invention incorporates a dedicated valve at the output portion of each of the channels, such incorporation additionally solves the problem of cross-contamination between the contents of first and second constituent channels of the network of channels regardless of which level of fluidic resistance each of such channels possesses in comparison with other channel(s).

The understanding of any of the embodiments of FIGS. 12, 13A, 14A (or related embodiments) will be further enhanced upon considering the principle according to which the fluidic sample of interest is entered/delivered to the microfluidic chip such as chip 1200, 1300, 1400, for example. To this end, the following discussion, presented in reference to FIGS. 15A, 15B, 15C, and 15D and in further reference to FIGS. 9, 10A, 10B, provides additional insights into the system of the invention and its principle of operation. FIGS. 15A, 15B, 15C, and 15D illustrate a portion of an embodiment of the system located upstream with respect to a cuvette of an individual, constituent channel of the microfluidic chip (such as the cuvette 910C, for example) and timed operation of this portion, leading to the filling of the individual cuvette with a fluidic sample of interest and locking of such sample in place to eliminate the spatial drift of the sample during the photometric measurement.

In particular, FIGS. 15A, 15B, 15C, and 15D schematically illustrate a "store and forward" well or individual volume 1510, which is located upstream with respect to and is fluidly connected with the inlet portion 910A of the individual channel of the microfluidic chip. Also shown is a multi-way fluidic valve 1520 preceding the will 1510, through which a fluidic connection is operably established from a pump (as shown by an arrow; for example, pneumatic pump or stored pressurized gas cylinder, configured to deliver, in operation of the system, an auxiliary fluid towards the well 1510 and then towards the cuvette 910C to form a pressure front 1010) to the well 1510 and further through the individual channel to the valve 960. The well 1510 is dimensioned to hold/enclose therein a sample volume required (as shown in FIG. 10B) for proper operation of an embodiment of the invention, and has its inlet or aperture 1510A covered by a flap portion 1510B.

Figure 15A:
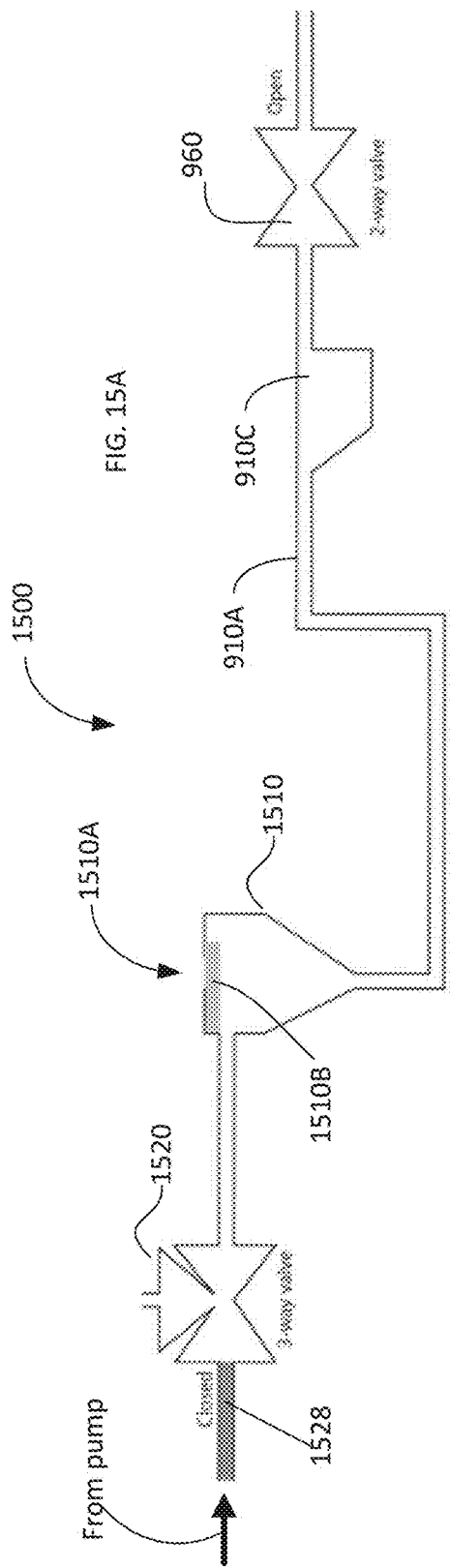

In one implementation, the flap portion is configured such as to substantially impenetrably seal the aperture of the well 1510, from inside the well, when the flap 1510B is in a rest position, see FIG. 15A. In other words, the flap 1510B is configured to substantially prevent a fluid from ingressing/egressing the volume of the well 1510 through the aperture 1510A connecting this volume with the ambient medium. (As will be understood from the further description, this embodiment of the well is preferably used with the 2-way version of the valve 1520, as discussed below). In a related embodiment, the flap 1510B is configured such as to provide for residual fluid seepage or leaking between the flap and the rims of the aperture 1510A in the direction from outside of the well 1510 to inside of the well 1510. (This embodiment is preferably used when the valve 1520 is configured as a 3-way valve, as shown below.) In either of the cases, however, the cooperation between the flap 1510B and the aperture 1510A is mechanically structured to sufficiently restrict the fluid flow out of the well 1510 and to have the pressure inside the well build up. The flap 1510B and the aperture 1510A are mechanically cooperated to ensure that—when the flap is in the rest position, covering the opening of the aperture to close the aperture—the residual flow of fluid through the aperture into the well is greater that the residual flow of fluid through the aperture out of the well. Generally, the flap 1510B can be structured as a elastomeric element (deformable within the limits of elastic deformation of the material of the flap, which may be, for example, a silicone rubber) or a rigid-material based spring-loaded flap (optionally complemented with a O-ring gasket disposed between the rigid flap and the rim of the aperture to improve sealing between the flap and the well 1510A; not shown). In the latter case, the spring loading the flap is configured to operate within the limits of its elastic deformation.

Figure 15B:
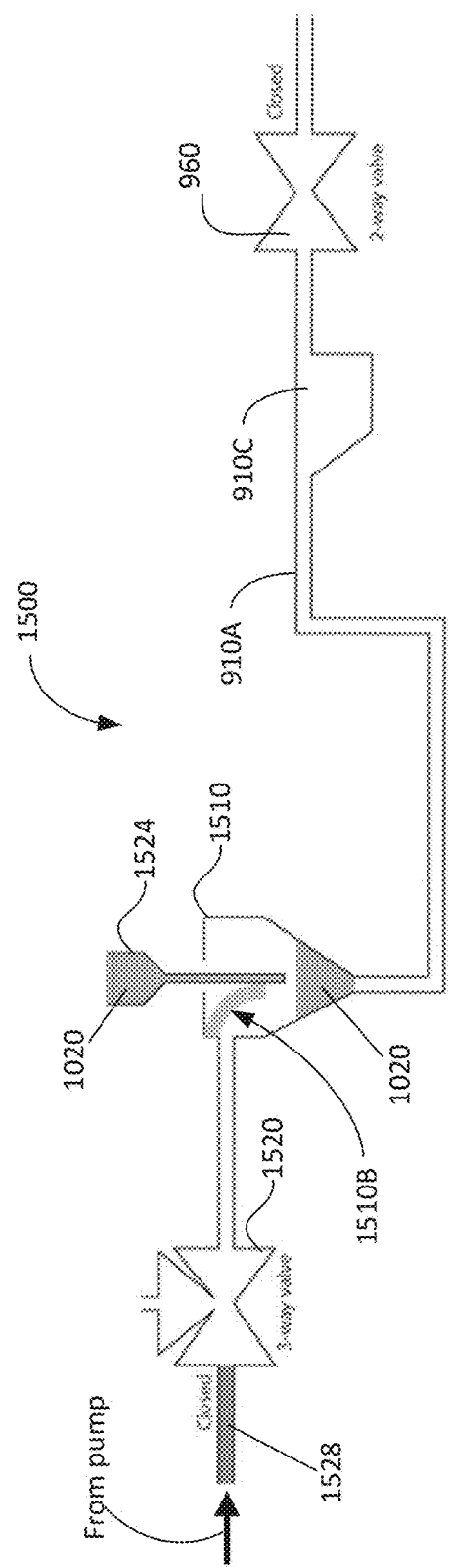

In operation, a sample of interest 1020 is delivered to the well 1510 through the aperture 1510A with a use of a pipette 1524 (of a robotic pipette system; not shown) that is judiciously inserted into the well 1510 through the aperture by forming a contact between the tip of the pipette 1524 to apply pressure to and appropriately deflect the flap 1520B, as shown in FIG. 15B. Before the insertion, the multi-way valve 1520 is kept closed to ensure that no fluidic pressure is delivered from the pump to the internal volume of the well

1510. Once the tip of the pipette 1524 is in the internal volume of the well 1510, a prescribed amount of the sample 1020 is added to the well 1510 while, at the same time, the multi-way valve 1520 is kept closed to block the propagation of the auxiliary fluid 1528 through the valve 1520 and towards the volume of the well 1510. Following the disbursement of the sample 1020 into the well 1510, the pipette 1524 is removed from the well 1510 to allow the flap 1510B to assume its rest position and substantially seal the aperture 1510A.

Now, in reference to FIG. 15C, the multi-way valve 1520 is opened to allow the pressurized auxiliary fluid 1528 (such as gas, for example) pass the valve 1524, fill the well 1510 while pushing the sample 1020 towards the inlet portion 910A of the individual microfluidic channel and further drive the sample 1020 into the cuvette 910C. The numeral 1530 indicates an interface between the fluid 1528 and the sample 1020, formed in an intermediate portion of the channel; leading to the cuvette 910C. The propagation of the fluids 1020, 1528 downstream (i.e., in a direction from the well 1510 towards the cuvette 910C) coincides with and is balanced by another fluid 1534 present in the system downstream from the cuvette and passing through the open valve 960.

In reference to FIG. 15D, once the sample 1020 has filled the cuvette 910C and has been delivered past the valve 960 while pushing the fluid 1534 downstream (as was already discussed in reference to FIG. 10B), the downstream valve 960 is closed to isolate the sample 1020 in the system. The "pinching" of the fluid path by the valve 960 prevents the sample 1020 from moving with respect to the cuvette 910C. At the same time, the upstream multi-way valve 1520 is partially closed/partially open, as shown in FIG. 15D, and due to the lack of continued entrance of the fluid 1528 into the system the pressure upstream of the sample drops substantially to a level of atmospheric pressure. Alternatively, as discussed above, the multi-way valve may continue to operate to continually apply the pressure 1010 to the sample 1020 to ensure the immobilization of the sample with respect to the cuvette and to store/preserve a level of pressure required for the removal of the sample from the cuvette upon the completion of the measurement. In this situation, the following after the photometric measurement step of removing the sample of the cuvette 910C requires a reduced amount of fluid 1528. In yet another related embodiment, the flap 1510B can be configured to not completely seal the aperture 1510A such that, after the valve 960 is closed, the flap seeps or oozes a bit to allow the fluidic pressure applied to the sample 1020 from upstream the cuvette to be substantially at an atmospheric pressure level. Generally, and according to the idea of the invention, a) in a situation when atmospheric pressure is sufficient to "lock the fluid sample in the cuvette", the pressure created upstream to move the fluid in the cuvette can be relieved, while b) when atmospheric pressure may be insufficient to "lock the fluid sample in the cuvette" or should the stored gas pressure be used to remove the fluid sample from the cuvette, the pressure created upstream with respect to the cuvette is maintained.

Figure 15E:
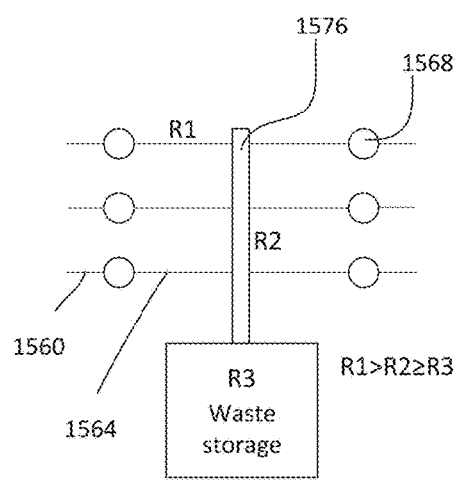
Figure 15F:
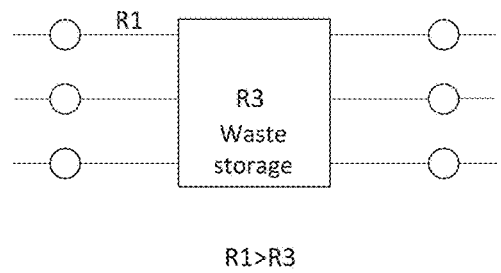
Figure 15G:
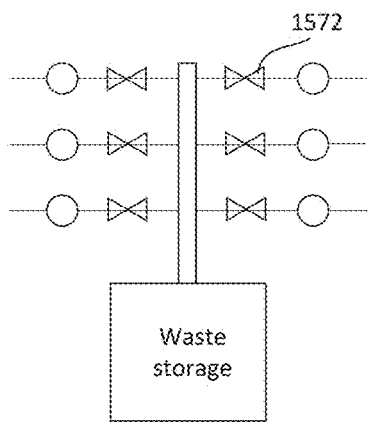
Figure 15H:
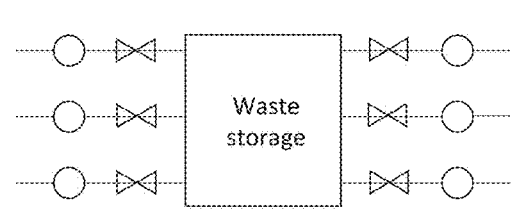

Additional illustrations to the implementation of concepts of the invention are provided by schematic diagrams of FIGS. 15E, 15F, 15G, and 15H, in which the inlet/outlet portions (such as those shown as 1560, 1564) of individual microfluidic channels are shown in solid lines, the cuvette portions (such as 1568) are shown with circles, the valves (such as 1572) are indicated with "bow-tie" indicia, and the main outlet channel portions (if present, such as 1576, delivering measured fluid samples from individual cuvettes to the common waste storage) are shown with wide stripe-shaped rectangles. Fluidic resistance of an i-th portion of a channel is indicated with Ri. In the schematics of FIGS. 15E and 15F, portions of channels characterized by $R_1$ are designed to act as capillary valve(s) for the cuvette(s), while the difference between $R_2$ and $R_3$ values is intended to be and is chosen to be, in practice, substantial enough to ensure that backflow into any of the channel portions with $R_1$ is eliminated (path of least resistance). In the embodiments structured according to the schematics of FIGS. 15G, 15H, channel portions with $R_1$ reduce flow rate (due to, for example, increased pressure drop that is a function of channel diameter and length) at any given input pressure, in addition to minimizing a volume of the sample used for the measurement. This improves the ability of the system to control the fluid through the valve with respect to utilizing the act of closing the valve in order to minimize the used fluid sample volume.

The operation of the embodiment(s) of the invention has been validated by photometrically measuring fluidic (blood) sample(s) contained in identified cuvette portion(s) of the channels and isolated fluidically from the rest of the system to simultaneously and independently-for-each-cuvette control the time-variable processes (assay chemistry) to determine the concentration of hemoglobin, glucose, and alkaline phosphatase (ALP). (Notably, the ability to control and govern and effectuate transfer of the fluid(s) through one channel or portion of the channel of the microfluidic chip independently from the process of transfer through another channel allows the user of the embodiment of the invention to carry out different measurements in different cuvettes at the same time or according to time-overlapping schedules— and regardless of the nature of the measurements. Different types of chemical reactions may take different times and may require different starting and/or processing conditions such as temperature, for instance. Non-limiting examples of such reactions are the rate reaction and enzymatic reaction. In case of inability of an embodiment of the invention to independently control the timings of delivery/holding/flushing of the samples through the individual channels, one of these two types of measurements would not be complete by the time another has already reached its termination point.)

Figure 16C:
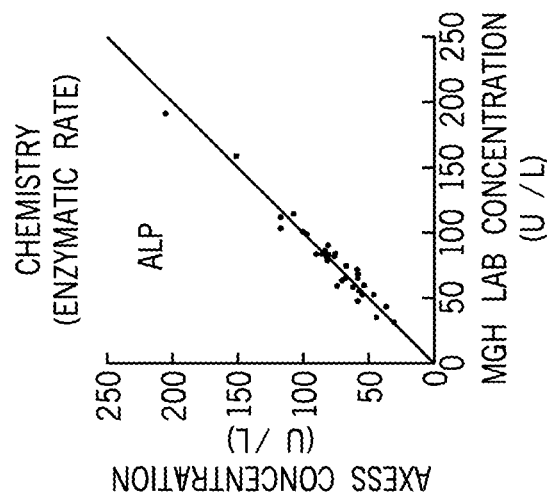
FIGS. 16A, 16B, and 16C contain plots representing results of empirical validation of the operation of a system of an embodiment of the invention and showing a comparison between the measurement results acquired with embodiment(s) of the invention and those provided by conventionally-used diagnostic equipment.
Figure 16B:
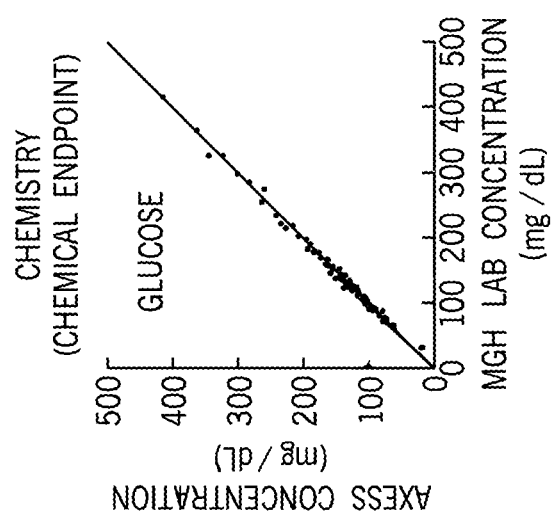
Figure 16A:
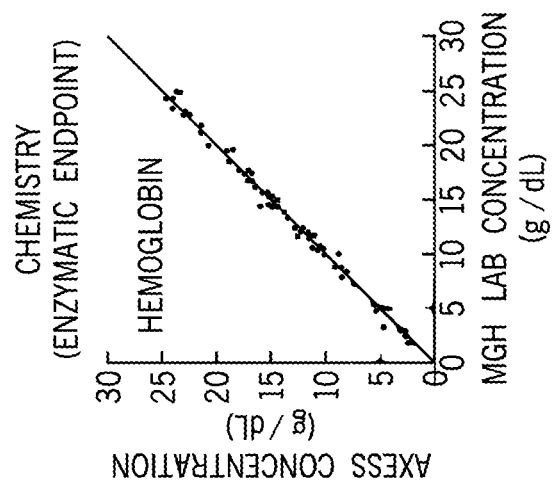

The same samples had been previously measured with the use of conventional clinical laboratory diagnostic equipment specifically, Abbott Architect c4000). The results of comparison between these two measurements are presented in FIGS. 16A, 16B, and 16C, where the results of a measurement carded out with conventional equipment are referred to the x-axes of the plots, while the results of the measurement with an embodiment of the present invention are referred to the y-axes of the plots. The exceptional performance of the system of the invention is evidenced not only by the substantial linearity of the comparison regardless of the value of concentration (mg/dL), but also by the fact that such linear dependencies are represented by straight lines inclined (with respect to x- or y-axes) by about 45 degrees. A person of skill in the art will immediately recognize that the coefficient of variation between the two instruments (or, the results of measurements conducted with the use of two methodologies) is substantially equivalent and is well within the values of experimental errors. The results achieved with the use of the methods of the present invention are statistically equivalent to those obtained with conventional equipment, as validated by a third party.

To effect the operation of an embodiment of the above-described IPM system (including the design of a multiplexed microfluidic chip according to the methodology described above) and performance of the steps required to acquire and process the photometric data representing results of the measurements of the fluid sample(s) passing through an individual cuvette of the IPM system may require the operation of a processor controlled by application-specific instructions stored in a tangible memory element. Those skilled in the art should readily appreciate that required algorithmical functions, operations, and decisions may be implemented as computer program instructions, software, hardware, firmware or combinations thereof. Those skilled in the art should also readily appreciate that instructions or programs defining the functions and elements of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable: storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Within this specification, embodiments have been described in a way that enables a clear and concise specification to be written, but it is intended and will be appreciated that embodiments may be variously combined or separated without parting from the scope of the invention. In particular, it will be appreciated that each of the features described herein is applicable to most if not all aspects of the invention.

The invention as recited in claims appended to this disclosure is intended to be assessed in light of the disclosure as a whole, including features disclosed in prior art to which reference is made.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The term substantially equivalent is used in the same fashion.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The disclosed embodiments of the invention discuss specific examples of isolation of multiple different sample chemistries within a single connected fluidic network, of design rules for optimizing physical characteristics of the measurement cuvettes and fluidic network, of design rules for cuvettes to be repeatedly used in a fluidic network (including sample loading without air bubbles and sample flushing without carryover contamination), and of performing simultaneous photometric measurements of (optionally multiple) samples at (optionally multiple) wavelengths in a consolidated package. Modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s). In addition, the terminology used herein is with the purpose of describing particular embodiments only, and is not intended to limit the scope of the present invention.

What is claimed is:

1. A microfluidic device comprising:
   first and second substrates integrated with one another along surfaces thereof to form a stack of substrates;
   a first microfluidic channel including first inlet portion, first cuvette portion, and first outlet portion,
       wherein at least one of said first inlet and outlet portions traverses both of said first and second substrates;
   a first fluidic valve in fluid communication with and fluidly connected to the outlet portion;
   a fluidic well disposed upstream with respect to the first cuvette portion in fluid communication with the first inlet portion,
       said fluidic well having an internal volume and an aperture connecting said internal volume with an ambient medium surrounding the fluidic well,
       said fluidic well equipped with a flap element dimensioned to reversibly close the aperture from inside the fluidic well when in a rest position, and to reversibly open said aperture in response to a force applied to the flap element from the ambient medium inwardly to the internal volume; and
   a second fluidic valve disposed upstream with respect to said well and configured to deliver an auxiliary fluid into the fluidic well along a channel connecting the second fluidic valve with the fluidic well.

2. The microfluidic device according to claim 1, wherein said first cuvette portion is dimensioned to prevent formation of an air-bubble therein when a first fluid sample is being delivered from the first inlet portion to the first cuvette portion.

3. The microfluidic device according to claim 1, further comprising a second microfluidic channel including second inlet portion, second cuvette portion, and second outlet portion, at least one of said second inlet and outlet portions extending across both the first and second substrates; and a main outlet channel fluidly connected to both the first and second inlet portions to receive a fluid sample from either of said first and second cuvette portions.

4. The microfluidic device according to claim 3, configured to ensure that transfer of fluid through the first microfluidic channel and transfer of fluid through the second microfluidic channel are independent from one another.

5. The microfluidic device according to claim 3, further comprising a storage volume in fluid communication with the main outlet portion to receive said fluid sample from either of the first and second cuvette portions through the main outlet channel.

6. The microfluidic device according to claim 3, wherein said main outlet channel penetrates both the first and second substrates.

7. The microfluidic device according to claim 1, further comprising a second microfluidic channel including a second inlet portion, a second cuvette portion, and a second outlet portion, at least one of said second inlet and outlet portions extending across both the first and second substrates; and a storage volume in fluid communication with the first and second outlet portions to receive a fluid sample from either of the first and second cuvette portions through the first and second outlet portions, respectively.

8. The microfluidic device according to claim 7, configured to ensure that transfer of fluid through the first microfluidic channel and transfer of fluid through the second microfluidic channel are independent from one another.

9. The microfluidic device according to claim 1, further comprising a third substrate in said stack, wherein at least two of the first, second, and third substrates are integrated with one another via a surface sealing layer, the surface sealing layer configured to fluidly seal a junction, wherein said junction is formed by at least one of the first inlet and outlet portions traversing said at least two of the first, second, and third substrates.

10. The microfluidic device according to claim 1, further comprising a light source configured to deliver a beam of light to said first cuvette; and an optical detector disposed in optical communication with said first cuvette such as to receive at least a portion of said beam that has traversed the first cuvette.

11. A microfluidic device comprising:

first and second substrates integrated with one another along surfaces thereof to form a stack of substrates;

a first microfluidic channel including first inlet portion, first cuvette portion, and first outlet portion, wherein at least one of said first inlet and outlet portions traverses both of said first and second substrates;

a first fluidic valve in fluid communication with and fluidly connected to the outlet portion;

a fluidic well disposed upstream with respect to the first cuvette portion in fluid communication with the first inlet portion, said fluidic well having an internal volume and an aperture connecting said internal volume with an ambient medium surrounding the fluidic well, said fluidic well equipped with a flap element dimensioned to reversibly close the aperture from inside the fluidic well when in a rest position, and to reversibly open said aperture in response to a force applied to the flap element from the ambient medium inwardly to the internal volume;

a second microfluidic channel including a second inlet portion, a second cuvette portion, and a second outlet portion, at least one of said second inlet and outlet portions extending across both the first and second substrates; and a main outlet channel fluidly connected to both the first and second inlet portions to receive a fluid sample from either of said first and second cuvette portions.

12. The microfluidic device according to claim 11, further comprising a second fluidic valve disposed upstream with respect to said fluidic well and configured to deliver an auxiliary fluid into the fluidic well along a channel connecting the second fluidic valve with the fluidic well.

13. The microfluidic device according to claim 11, configured to ensure that transfer of fluid through the first microfluidic channel and transfer of fluid through the second microfluidic channel are independent from one another.

14. The microfluidic device according to claim 11, further comprising a storage volume in fluid communication with the main outlet portion to receive said fluid sample from either of the first and second cuvette portions through the main outlet channels.

15. The microfluidic device according to claim 11, wherein said main outlet channel penetrates both the first and second substrates.

16. The microfluidic device according to claim 11, further comprising a third substrate in said stack, wherein at least two of the first, second, and third substrates are integrated with one another via a surface sealing layer, the surface sealing layer configured to fluidly seal a junction, wherein said junction is formed by at least one of the first inlet and outlet portions traversing said at least two of the first, second, and third substrates.

17. The microfluidic device according to claim 11, further comprising a light source configured to deliver a beam of light to said first cuvette; and an optical detector disposed in optical communication with said first cuvette such as to receive at least a portion of said beam that has traversed the first cuvette.

18. A microfluidic device comprising:

first and second substrates integrated with one another along surfaces thereof to form a stack of substrates;

a first microfluidic channel including first inlet portion, first cuvette portion, and first outlet portion, wherein at least one of said first inlet and outlet portions traverses both of said first and second substrates;

a first fluidic valve in fluid communication fluidly connected to the outlet portion;

a fluidic well disposed upstream with respect to the first cuvette portion in fluid communication with the first inlet portion, said fluidic well having an internal volume and an aperture connecting said internal volume with an ambient medium surrounding the fluidic well, said fluidic well equipped with a flap element dimensioned to reversibly close the aperture from inside the fluidic well when in a rest position, and to reversibly open said aperture in response to a force applied to the flap element from the ambient medium inwardly to the internal volume;

a second microfluidic channel including a second inlet portion, a second cuvette portion, and a second outlet portion, at least one of said second inlet and outlet portions extending across both the first and second substrates; and a storage volume in fluid communication with the first and second outlet portions to receive a fluid sample from either of the first and second cuvette portions through the first and second outlet portions, respectively.

19. The microfluidic device according to claim 18, further comprising a second fluidic valve disposed upstream with respect to said fluidic well and configured to deliver an auxiliary fluid into the fluidic well along a channel connecting the second fluidic valve with the fluidic well.

20. The microfluidic device according to claim 18, wherein said first cuvette portion is dimensioned to prevent formation of an air-bubble therein when the first fluid sample is being delivered from the first inlet portion to the first cuvette portion.

21. The microfluidic device according to claim 18, further comprising
a main outlet channel fluidly connected to both the first and second inlet portions to receive a fluid sample from either of said first and second cuvette portions.

22. The microfluidic device according to claim 21, configured to ensure that transfer of fluid through the first microfluidic channel and transfer of fluid through the second microfluidic channel are independent from one another.

23. The microfluidic device according to claim 21, further comprising a storage volume in fluid communication with the main outlet portion to receive said fluid sample from either of the first and second cuvette portions through the main outlet channels.

24. The microfluidic device according to claim 21, wherein said main outlet channel penetrates both the first and second substrates.

25. The microfluidic device according to claim 18, configured to ensure that transfer of fluid through the first microfluidic channel and transfer of fluid through the second microfluidic channel are independent from one another.

26. The microfluidic device according to claim 18, further comprising a third substrate in said stack, wherein at least two of the first, second, and third substrates are integrated with one another via a surface sealing layer, the surface sealing layer configured to fluidly seal a junction,
wherein said junction is formed by the at least one of the first inlet and outlet portions traversing said at least two of the first, second and third substrates.

27. The microfluidic device according to claim 18, further comprising
a light source configured to deliver a beam of light to said first cuvette; and
an optical detector disposed in optical communication with said first cuvette such as to receive at least a portion of said beam that has traversed the first cuvette.

* * * * *

UNITED STATES PATENT AND TRADEMARK OFFICE
CERTIFICATE OF CORRECTION

| | |
|---|---|
| PATENT NO. | : 10,215,687 B2 |
| APPLICATION NO. | : 15/677459 |
| DATED | : February 26, 2019 |
| INVENTOR(S) | : Ramin Haghgooie et al. |

It is certified that error appears in the above-identified patent and that said Letters Patent is hereby corrected as shown below:

In the Specification

Column 18, Line 4, "9200" should be --920C--.

Column 20, Line 25, "12100" should be --1210C--.

Column 24, Line 49, "carded" should be --carried--.

Signed and Sealed this
Seventh Day of May, 2019

Andrei Iancu
*Director of the United States Patent and Trademark Office*